(12) United States Patent
Abu-Tarif et al.

(10) Patent No.: US 10,772,510 B2
(45) Date of Patent: Sep. 15, 2020

(54) VITAL SIGNS MONITOR FOR CONTROLLING POWER-ADJUSTABLE EXAMINATION TABLE

(75) Inventors: Asad Ahmad Abu-Tarif, Irvine, CA (US); Robert Allan Menke, Versailles, OH (US); Kim M. Noone, Redondo Beach, CA (US)

(73) Assignee: Midmark Corporation, Versailles, OH (US)

( * ) Notice: Subject to any disclaimer, the term of this patent is extended or adjusted under 35 U.S.C. 154(b) by 943 days.

(21) Appl. No.: 13/592,190

(22) Filed: Aug. 22, 2012

(65) Prior Publication Data

US 2014/0058213 A1 Feb. 27, 2014

(51) Int. Cl.
*A61B 5/0205* (2006.01)
*A61B 5/1455* (2006.01)
*A61B 5/021* (2006.01)
*A61B 5/00* (2006.01)

(52) U.S. Cl.
CPC .......... *A61B 5/0205* (2013.01); *A61B 5/0002* (2013.01); *A61B 5/021* (2013.01); *A61B 5/1455* (2013.01)

(58) Field of Classification Search
CPC ..... A61B 5/0002; A61B 5/0205; A61B 5/021; A61B 5/1455
See application file for complete search history.

(56) References Cited

U.S. PATENT DOCUMENTS

| 3,845,945 A | * | 11/1974 | Lawley | A61G 15/005 297/325 |
| 4,934,468 A | * | 6/1990 | Koerber, Sr. | G01G 19/445 128/897 |
| 4,998,939 A | * | 3/1991 | Potthast | A61G 7/0507 5/424 |
| 5,451,747 A | * | 9/1995 | Sullivan | A61F 7/007 219/505 |
| 5,724,025 A | | 3/1998 | Tavori | |

(Continued)

OTHER PUBLICATIONS

Welch Allyn Connex Integrated Wall System; printed from http://www.welchallyn.com/documents/EENT/Connex_IWS/Connex_Integrated_Wall_System_AMB_WR.pdf; printed on Aug. 30, 2012.
Welch Allyn Connex Integrated Wall System; printed from http://www.welchallyn.com/documents/EENT/Connex_IWS/Connex_Integrated_Wall_System_Acute_WR.pdf; printed on Aug. 30, 2012.

(Continued)

*Primary Examiner* — Michael W Kahelin
*Assistant Examiner* — Vynn V Huh
(74) *Attorney, Agent, or Firm* — Frost Brown Todd LLC

(57) ABSTRACT

The present invention pertains to devices and methods for increasing the ease of data gathering and efficiency of information flow in a clinical setting. The devices of the present invention comprise medical examination tables, dental examination chairs and vital signs monitors, all of which further comprise integrated hardware and software that allow these devices to effectively collect and communicate data in a manner that allows for greater ease of use of these devices and subsequent increased efficiency in the clinical space on the part of the clinician. The medical examination tables and dental examination chairs of the present invention preferably include at least one load sensor for measuring a subject's weight when the subject is seated thereon. The methods of the present invention are directed at using the aforementioned devices to increase ease of data collection and efficiency of care delivery within a space in which the devices are used.

6 Claims, 13 Drawing Sheets

(56) References Cited

U.S. PATENT DOCUMENTS

| | | | |
|---|---|---|---|
| 5,801,914 A * | 9/1998 | Thrash | H05B 3/342 |
| | | | 219/212 |
| 5,861,582 A * | 1/1999 | Flanagan | G01G 3/13 |
| | | | 177/144 |
| 5,864,901 A * | 2/1999 | Blumel | 5/610 |
| 7,021,315 B1 * | 4/2006 | Szymanik | A61B 90/60 |
| | | | 128/845 |
| 7,154,397 B2 | 12/2006 | Zerhusen et al. | |
| 7,350,249 B2 | 4/2008 | Jacobs et al. | |
| 7,390,299 B2 | 6/2008 | Weiner et al. | |
| 7,513,000 B2 | 4/2009 | DeBraal et al. | |
| 7,679,520 B2 | 3/2010 | Zerhusen et al. | |
| 7,845,033 B2 | 12/2010 | DeBraal et al. | |
| 7,911,349 B2 | 3/2011 | Zerhusen et al. | |
| 7,990,691 B2 | 8/2011 | Clark et al. | |
| 8,096,006 B2 | 1/2012 | DeBraal et al. | |
| RE43,532 E | 7/2012 | Menkedick et al. | |
| 8,430,451 B1 * | 4/2013 | Heinz | B60N 2/286 |
| | | | 297/180.12 |
| 8,763,178 B1 * | 7/2014 | Martin | A61G 13/06 |
| | | | 5/11 |
| 2002/0014951 A1 * | 2/2002 | Kramer et al. | 340/5.8 |
| 2002/0044059 A1 | 4/2002 | Reeder et al. | |
| 2002/0099409 A1 * | 7/2002 | Hui | 606/201 |
| 2003/0074735 A1 * | 4/2003 | Zachrisson | 5/607 |
| 2004/0054261 A1 | 3/2004 | Kamataki et al. | |
| 2004/0202289 A1 * | 10/2004 | Settergren | A61B 6/04 |
| | | | 378/209 |
| 2006/0179571 A1 * | 8/2006 | Newkirk | 5/600 |
| 2007/0258334 A1 * | 11/2007 | Chiang et al. | 368/10 |
| 2008/0132383 A1 * | 6/2008 | Einav et al. | 482/8 |
| 2008/0234555 A1 * | 9/2008 | Lafleche | A61B 5/00 |
| | | | 600/300 |
| 2008/0235875 A1 * | 10/2008 | Wells | 5/602 |
| 2009/0009284 A1 * | 1/2009 | Sako | 340/5.82 |
| 2010/0048984 A1 * | 2/2010 | Anderson | 600/27 |
| 2010/0198120 A1 * | 8/2010 | Tago | A61H 1/0237 |
| | | | 601/134 |
| 2011/0030141 A1 * | 2/2011 | Soderberg et al. | 5/600 |
| 2011/0112442 A1 * | 5/2011 | Meger et al. | 600/595 |
| 2012/0036638 A1 * | 2/2012 | Penninger et al. | 5/610 |
| 2012/0078144 A1 * | 3/2012 | Sinykin | 601/148 |
| 2012/0102434 A1 | 4/2012 | Zerhusen et al. | |
| 2012/0186018 A1 | 7/2012 | DeBraal et al. | |
| 2012/0299353 A1 * | 11/2012 | Griswold | A61G 5/10 |
| | | | 297/354.1 |
| 2013/0019408 A1 * | 1/2013 | Jacofsky et al. | 5/613 |
| 2013/0046155 A1 * | 2/2013 | Marasco | 600/323 |

OTHER PUBLICATIONS

Welch Allyn Connex Vital Signs Monitor; printed from http://www.welchallyn.com/apps/products/product.jsp?id=19-pe-96-1276872488099; printed on Aug. 30, 2012.

Welch Allyn Spot Vital Signs; printed from http://www.welchallyn.com/documents/Patient%20Monitoring/Vital%20Signs%20Capture/Spot%20Vital%20Signs/SM2382_RevF_20101207_Spot_Vital_Signs.pdf; printed on Aug. 30, 2012.

Welch Allyn Spot Vital Signs LXi; printed from http://www.welchallyn.com/documents/Patient%20Monitoring/Vital%20Signs%20Capture/Spot%20Vital%20Signs%20LXi/productbrochure_20080228_spotlxiwireless.pdf; printed on Aug. 30, 2012.

Welch Allyn Vital Signs Monitor 300 Series; printed from http://www.welchallyn.com/documents/Patient%20Monitoring/Continuous%20Monitoring/Vital%20Signs%20Monitor%20300%20Series/productbrochure_20070323_vsm300.pdf; printed on Aug. 30, 2012.

Brewer Access High-Low Exam Table; printed from http://www.brewercompany.com/BrewerCompanyFilePile/Literature-Downloads1/AccessHighLowExamTable.pdf; printed on Aug. 30, 2012.

Brewer Assist PRO and Brewer Assist Power Procedure Table; printed from http://www.brewercompany.com/BrewerCompanyFilePile/Literature-Downloads1/AssistPowerProcedureTables.pdf; printed on Aug. 30, 2012.

\* cited by examiner

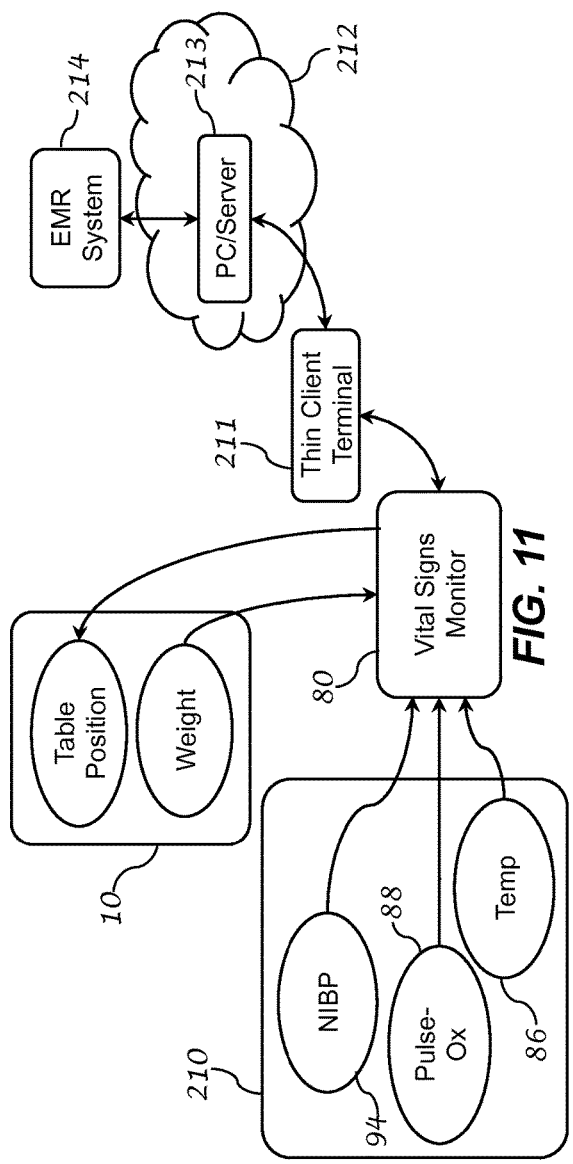
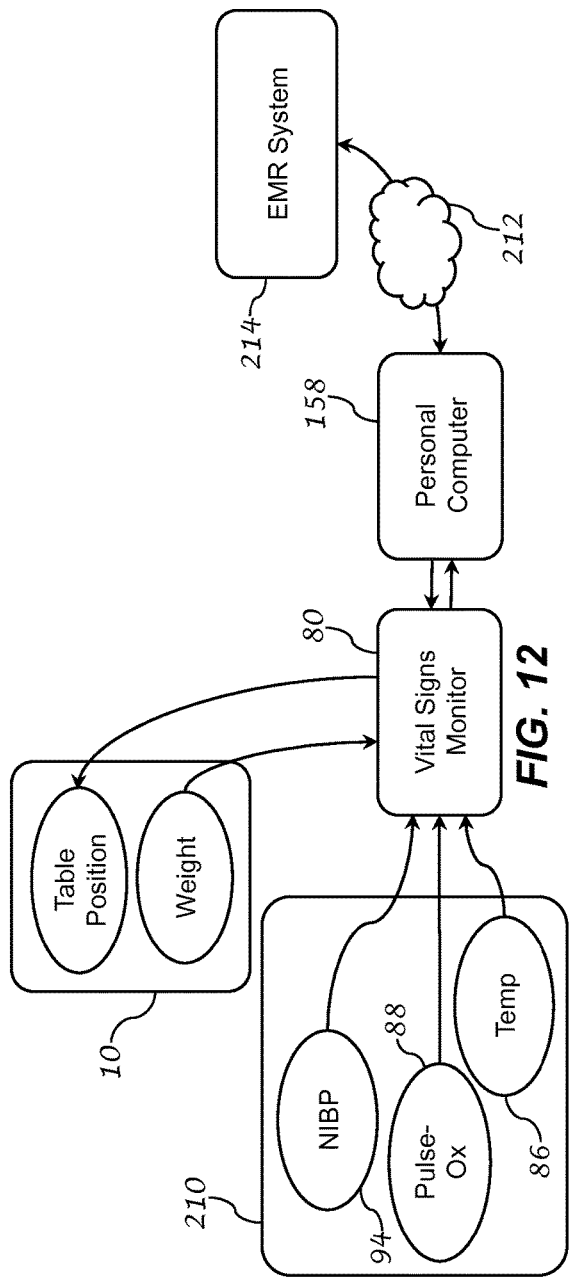

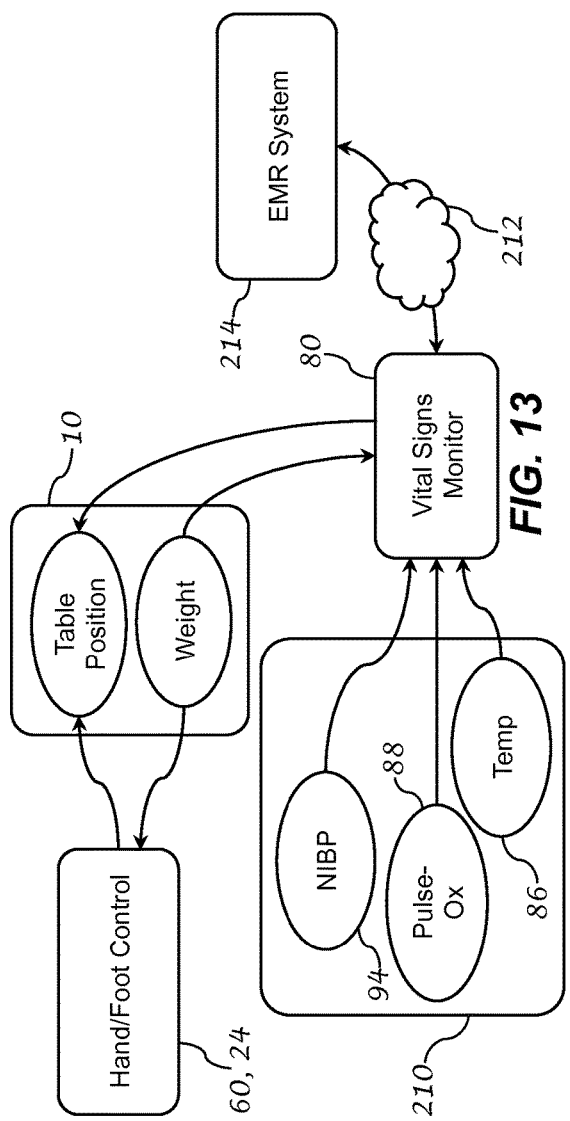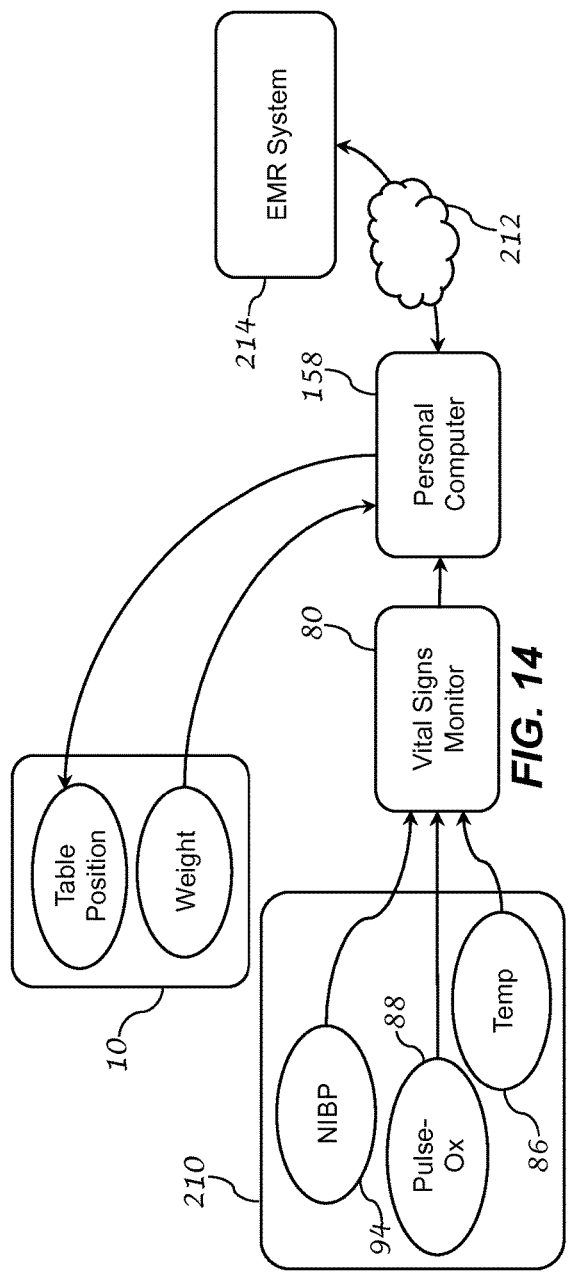

VITAL SIGNS MONITOR FOR CONTROLLING POWER-ADJUSTABLE EXAMINATION TABLE

BACKGROUND OF THE INVENTION

The medical exam table, medical procedure chair, and dental exam chair lie at the center of the patient care experience in nearly all outpatient clinical settings. Traditionally, these items have been used solely for their outward utilitarian benefit—that is, solely to support and position a patient for a medical or dental procedure or examination. Recognizing the need for medical and dental tables and chairs that provide greater functionality and efficiency to the clinical space, the present invention is broadly directed to medical and dental tables and chairs that include an integrated scale for determining a subject's weight and a processing system that allows these tables and chairs to communicate with and be controlled by a vital signs monitor. The present invention is thus further directed to vital signs monitors that are capable of receiving weight measurements obtained from the aforementioned medical and dental tables and chairs, as well as controlling the position of these tables and chairs. While the breadth and depth of the present invention is described in greater detail below, it is useful from a background perspective to understand certain shortcomings that currently exist in the clinical space that would be effectively addressed through implementation of the present invention.

Presently, when a subject enters a clinical space for an examination or other medical or dental treatment or procedure, the subject is frequently weighed on a common scale located in a common area of the clinical space. Not only is such a practice often uncomfortable for a subject who is self-conscious regarding his or her weight, but it is also inefficient since weighing of the subject constitutes a separate step that must be performed by the clinician. Additionally, it is often also the case that the clinician must perform the time-consuming step of manually entering the subject's weight into the clinician's records. Furthermore, once a subject enters the examination or treatment room, the clinician must generally obtain certain vital signs from the subject and is then required to properly position the examination table or chair once the subject is seated thereon before being able to begin treatment or examination of the subject.

Given the above-noted observations, the present invention is directed to medical and dental exam tables and chairs that include an integrated weight scale and is also directed to vital signs monitors capable of connecting to, controlling, and communicating with these medical and dental exam tables and chairs. By providing such devices, efficiency of data collection, uniformity and efficacy of clinical treatment, and the patient's clinical experience can be greatly enhanced.

BRIEF SUMMARY OF THE INVENTION

The present invention relates to devices and methods, which, from a high-level perspective, serve to increase the ease of data gathering and information flow in a clinical setting. By way of brief summary, the devices of the present invention include, but are not limited to, medical exam tables, dental exam chairs and vital signs monitors, all of which further include integrated hardware and software that allow these devices to effectively collect data and communicate one with another in a manner that allows for greater ease of use of these devices and increased efficiency in the clinical space on the part of the clinician. The methods of the present invention are directed at using the aforementioned devices to increase ease of data collection and efficiency of care delivery within a space in which the devices are used.

As a brief example of how the present invention may be utilized, in one of its preferred embodiments the present invention includes a power-adjustable medical exam table with an integrated scale and a vital signs monitor capable of connecting to and communicating with the power-adjustable medical exam table. In this example the vital signs monitor includes appropriate hardware and software to allow it to control positioning of the medical exam table. Further, the vital signs monitor of this example, in addition to being capable of measuring traditional vital signs from a subject, is also capable of capturing a weight measurement produced by the exam table and then transmitting this and other measurements to an electronic medical record system for recording. Continuing this example, a subject may enter a treatment room at a medical clinic and be seated on the medical examination table of the present invention, near which is positioned a vital signs monitor of the present invention. The exam table then automatically measures the subject's weight and sends this weight to the vital signs monitor, which is connected to the examination table. A clinician then further utilizes the vital signs monitor of the present invention as a control point to properly position a subject for obtaining a measurement of the subject's blood pressure using the vital signs monitor. After a blood pressure measurement is obtained, the vital signs monitor of the present invention sends both the subject's weight and the subject's blood pressure measurements to the subject's electronic medical record for recording.

While a number of more specific examples and a full description of the present invention are provided below, the example provided directly above should nevertheless be sufficient to allow one of ordinary skill in the art to appreciate the fundamental scope and objects of the present invention as well as to quickly gain a summary understanding of the utility provided by the devices and methods of present invention.

BRIEF DESCRIPTION OF THE DRAWINGS

FIG. 11 A flow diagram illustrating one method of data movement between various elements of the present invention.

FIG. 12 A flow diagram illustrating one method of data movement between various elements of the present invention.

FIG. 13 A flow diagram illustrating one method of data movement between various elements of the present invention.

FIG. 14 A flow diagram illustrating one method of data movement between various elements of the present invention.

DETAILED DESCRIPTION OF THE INVENTION

Figure 1:
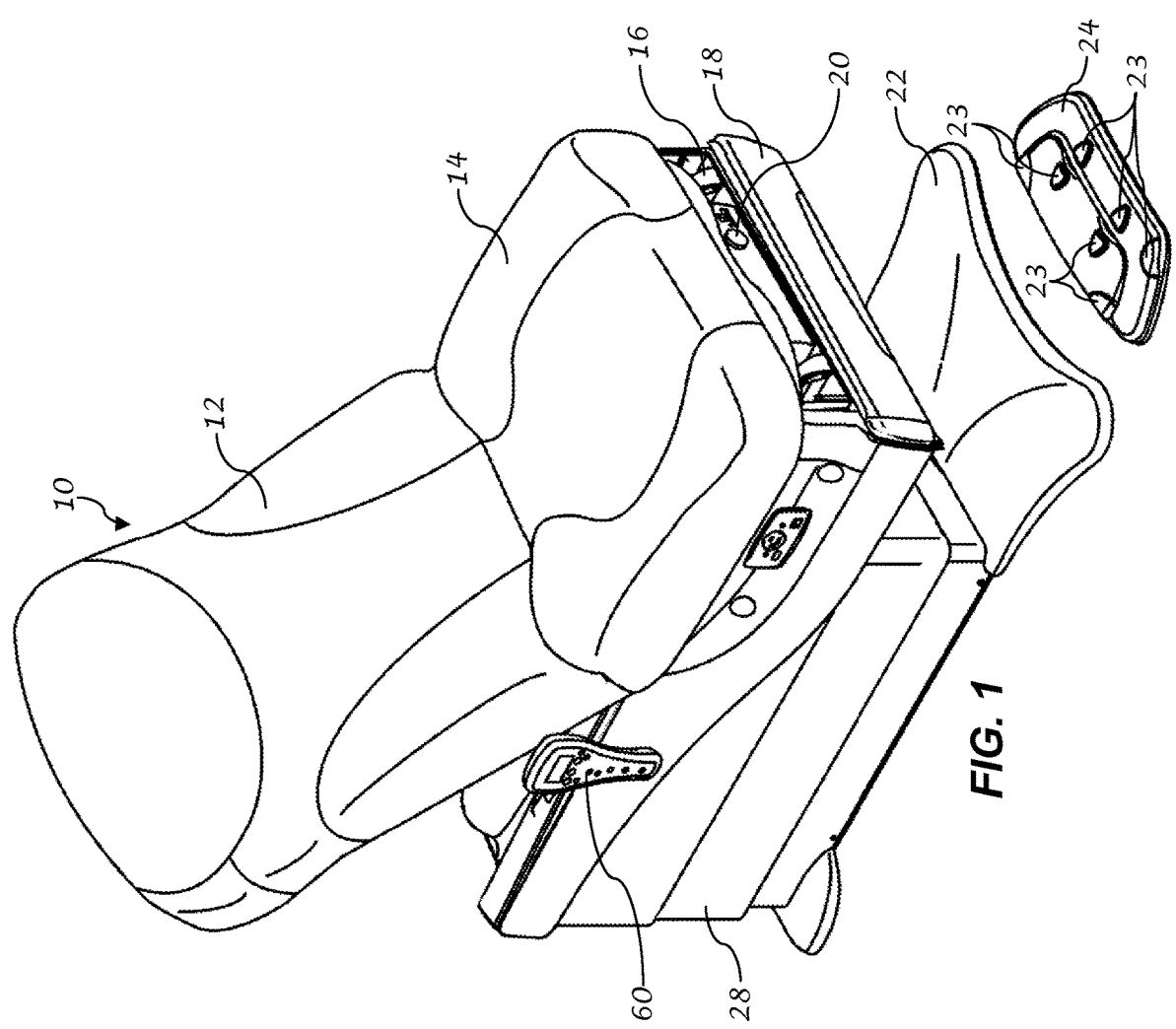
FIG. 1 Perspective drawing of one embodiment of the exam table of the present invention.

The present invention is directed to devices and methods for use and control of a power-adjustable examination table. The present invention is also directed to a device for monitoring a subject's vital signs and methods of use of this device alone and in combination with the aforementioned examination table.

Broadly stated, the present invention provides a vital signs monitor and examination table capable of communicating and transferring information one with the other. The present invention also provides methods of using the devices disclosed herein to allow a clinician to efficiently and effectively collect physiological information from a subject. Clinician as used herein refers to one whose specialized skill set allows them to competently participate in providing medical or dental care to a subject. Accordingly, clinician as used herein includes registered nurses, medical doctors, medical assistants, physician's assistants, nurse practitioners, dental hygienists, dental doctors (i.e. dentists), dental assistants, and the like.

To assist in clearly and effectively describing the various components of the present invention, it is helpful to broadly divide the invention into several elements. For purposes of describing the present invention these elements can be most easily broken down as (1) an examination table and (2) a vital signs monitor. Each of these elements will be described individually in greater detail below. It will be understood, however, that this categorical division of the present invention is intended only to aid in describing the invention and is not necessarily reflective of a required division of the above-noted elements when actually using the invention or practicing the associated methods.

The present invention is directed in part to an examination table. For purposes of this disclosure, an examination table is a medical or dental examination table or chair used to support or position a subject's body, or a portion of a subject's body, during an outpatient medical or dental procedure, examination, or consultation. By way of example, but not limitation, the medical or dental exam table or chair of the present invention can include dental exam and operatory chairs and medical tables and chairs for various uses and of various styles. These tables and/or chairs can be either multi-purpose or specialty-specific. Specialty-specific tables and/or chairs can include tables and/or chairs for specialties such as oral surgery, pediatrics, podiatry, plastic surgery, orthodontics, dermatology, and gynecology, among others. For simplicity, medical or dental exam tables or chairs as referenced above will hereinafter be collectively referred to as an exam table, unless otherwise noted.

In certain preferred embodiments of the present invention the exam table is adjustable. By adjustable it is meant that the table can be adjusted, where applicable, in any or all of height, degree of incline of the back support, degree of incline of the foot support, height of foot support, angle of the sitting area, or overall angle of the exam table. By degree of incline of the back support it is meant the angle of the back support relative to the sitting area. By angle of the sitting area and overall angle of the exam table it is meant the angle of the sitting area and/or exam table with respect to the surface on which the exam table is placed. For purposes of this disclosure, the Tait-Bryan convention will be used to describe table angles. Accordingly, adjustment of the angle of the sitting area or angle of the overall exam table refers to adjustment of the elevation and/or bank of the sitting area or overall exam table relative to the surface on which the table is placed. Adjustment of the exam table can be accomplished through power-driven adjustment, such as with a hydraulic or mechanical actuator or the like, by manual adjustment, or a combination of the two. Hereinafter, power-adjustable exam table will be used to refer to an exam table that is adjusted or moved at least in part by power-driven adjustment, such as with a hydraulic or mechanical actuator or the like. If the exam table is adjustable in height, this adjustment is preferably accomplished through the use of a scissors mechanism driven by a linear actuator. Although in other embodiments of the present invention this adjustment could be performed by simply using a linear actuator alone, without the use of a scissors mechanism.

In various preferred embodiments, the exam table of the present invention also includes sensors built into or attached to the table capable of sensing a current position of the table and transmitting this position to a processor that is part of the table and/or to another device. One example of such a sensor is a limit switch designed to prevent the exam table from being adjusted beyond certain predetermined stop points. Still other sensors include sensors for determining if an obstruction is interfering with movement of the table. For example if a user unintentionally places an appendage in such a way as to interfere with exam table movement, force sensors or optical sensors can be used to stop movement of the exam table and prevent user injury. Still further, in embodiments of the present invention in which the exam table is moved using linear actuators driven by electric motors, hall effect sensors can be used in combination with the electric motors to determine the number and direction of motor rotations and thus provide a method of accurately tracking table position.

In still other preferred embodiments the exam table of the present invention can include certain accessories or features that increase the ease and efficiency of examination procedures, management of the clinical space, or patient comfort, such as storage space built into the table, heated seating and/or storage areas, or tool rests extending from and attached to the table for holding tools or other accessories used in procedures performed. Examples of tools and other accessories usable with the exam table include exam lights capable of being attached to the table, IV poles, instrument trays, and arm rests or armboards for proper positioning of a subject's arm(s) for procedures such as the taking of blood pressure, collection of blood sample(s), or performance of outpatient surgical procedures. Still other items that can be used in connection with the exam table of the present invention include specific types of light sources such as those used in ophthalmology exams (e.g., blue light source, slit lamp, etc.), dermatological treatments (e.g., photodynamic therapy, laser therapy, etc.), or UV-based light sources such as those used in combination with light-curing adhesives or those used in dermatological procedures that involve treatment of a subject's skin with UV radiation. In still other embodiments, the exam table disclosed herein can be used as a mounting or positioning point for X-ray emitting devices used for conducting radiographic imaging, or ultrasound emitting devices used for ultrasonic imaging or other ultrasound-based procedures. Of the above-listed tools and other accessories, many are preferably attached directly to or directly supported by the exam table and can in certain preferred embodiments be optionally powered through the exam table via power sources located within or on the exam table. Power sources located within or on the exam table can include line voltage outlets, such as standard wall outlets and can also include low voltage power sources such as that provided by a universal serial bus port, or the like. Power provided through the table can be either alternating current or direct current power.

In still other preferred embodiments of the present invention, the exam table can serve as a connection point for certain diagnostic or measurement devices. Examples of such devices include devices for examining cardiac function, such as by ECG, or devices for examining pulmonary or respiratory function, such as by spirometry. In such instances the device can be powered through the exam table as well as optionally transfer data using hardware located within the exam table. Allowing connection of diagnostic devices to the exam table is beneficial because it can eliminate the need for additional independent connection points for such devices within an exam room or clinical space, by providing a single location for connection of all devices.

In yet other preferred embodiments, the exam table of the present invention includes a processing system. By processing system it is meant a system that is capable of receiving, generating, handling, storing and/or manipulating data. Thus, the exam table of the present invention preferably includes at least a microprocessor, a memory, and input and output ports or channels for sending and receiving data. The memory, in addition to being capable of storing data generated by the processor or received via the input port(s), is used to store instructions including commands and processes followed by the processor in controlling adjustment of the table and other table features as detailed below. The exam table memory is preferably digital memory capable of storing digitized data. The exam table memory is also preferably at least partially comprised of non-volatile digital memory.

The input and output port(s), or communications port(s), of the exam table can preferably send and receive data to and from the exam table by either wired or wireless transmission or a combination of the two and can handle and produce either digital or analog data. Examples of different types of communications ports include, but are not limited to, serial ports (e.g., various types registered jack ports such as RJ11 or RJ45 format using RS232, IEEE 802.3, or other similar communication standards), universal serial bus (USB) ports, and radio frequency (RF) network interface controllers with their associated antennas (hereinafter, wireless ports). Where appropriate, the input and output port(s) of the exam table are capable of interacting with and transmitting data between a number of different other processing systems connected through any type of network, including, for example, local area networks (LAN), personal area networks (PAN) and the Internet. If wireless transmission of data is implemented through a wireless port, it is preferable that the exam table includes hardware that allows the exam table to communicate wirelessly using any desired or appropriate protocol. Examples of protocols that could be used by the exam table to communicate wirelessly through a communication port include, but are not limited to, the Wireless Medical Telemetry Bands, in the 608-614 MHz, 1395-1400 MHz, or 1427-1432 MHz ranges, as well as ZigBee®, Bluetooth®, or IEEE 802.11 communication protocols.

In certain preferred embodiments of the present invention the exam table can have more than one communications port. In embodiments of the present invention that use multiple communications ports, it is not required that all ports be of the same type. For example, in certain preferred embodiments, the exam table may have multiples of each of USB ports, Ethernet ports, serial ports, and wireless ports, or such other ports as may be desirable for communication of analog or digital data. Multiple communications ports allow the exam table to both send and receive information more effectively and efficiently as well as to easily communicate with a number of different devices. By way of example, one can envision a scenario in which the exam table is simultaneously connected to both a USB-based device and a device that connects wirelessly to the exam table using an RF transceiver. While a more complete explanation of the capability of the exam table to interact with and send and receive data to and from various other devices is provided below, the above examples nevertheless serve well to provide a fundamental understanding of the intended scope of the capabilities of the exam table of the present invention.

In certain preferred embodiments of the present invention, the exam table is capable of sensing the weight of a subject seated on the exam table. This is preferably accomplished using a load sensor or a plurality of load sensors positioned within the table in such a manner that the output of these sensors can be used to determine the weight of a subject when the subject sits on the table. The weight sensor preferably consists of at least one load sensor capable of producing or modulating an electrical signal that changes in proportion to the weight supported by the sensor. For example, one preferred form of load sensor is a load cell that uses a series of resistors arranged in a Wheatstone bridge configuration. In this arrangement, changes in weight supported by the load cell (e.g. when a patient is seated on the exam table) lead to changes in resistance. These changes in resistance are measured and then processed to yield a determination of weight as a measurement of pound force. If more than one load cell is used, the processing system of the exam table can accept input from each load cell and then use summing, averaging, and other algorithms to accurately determine the weight of a subject seated on the table. Once a subject's weight is obtained using the at least one load cell and the processing system of the exam table, this weight can then be communicated to other devices connected to the exam table and potentially to other locations remote from the exam table using the various forms of networks described above.

As mentioned above, in certain preferred embodiments, the exam table of the present invention is adjustable by power driven adjustment through the use of various actuators and the like. These actuators and other power-driven adjustment features are preferably controlled via the processing system of the exam table. Because the processing system of the exam table can accept input from external devices, external devices can be used to accept input from a user of the table and allow the user to control the table. This input can then be used to control the positioning of the exam table. In this way, a user can conveniently control the position of an adjustable table using an external device. In various preferred embodiments of the present invention, the external device used to control the positioning of the exam table is a handheld control. This handheld control can include various buttons or other input mechanisms to allow the user to make desired adjustments to the position of the table. In other preferred embodiments, the handheld control can also include the ability, in combination with the processing system of the exam table, to assign certain buttons or other inputs on the handheld control to specific table positions. In this way, the user of the exam table can quickly position the exam table in an easily repeatable manner. In still other embodiments, the external device used to control positioning of the exam table is a foot-operated control wherein the user can adjust the position of the table by depressing buttons or other input mechanisms with his or her feet. As with the above-described handheld control, the foot-operated control can provide the ability to preset certain table positions and then easily return to these table positions when needed by selecting a preset position from the foot control interface. In both the handheld and foot-operated versions of the external control, the control unit can be connected to the table using either a wired or wireless connection of the types described herein. Furthermore, the external control can, in certain embodiments, include a display area where the weight measurement produced by an exam table capable of measuring a subject's weight can be displayed to the user of the table.

In addition to the above-noted features, the exam table preferably also includes a power source for powering the processing system of the exam table as well as providing power, where needed, to the sensors, actuators, and/or other devices used in combination with the exam table. Because of the power demands of the table, the power source is preferably line voltage (e.g. 120V, 60 Hz A/C; 220V, 50 Hz A/C) filtered through appropriate regulators so as to provide the correct level of power to the various component parts of the exam table.

As mentioned above, certain preferred embodiments of the present invention involve the use of a vital signs monitor (hereinafter "VSM"). As used herein, VSM refers to a device that is designed to be used in an ambulatory or outpatient setting and is capable of measuring any or all of a subject's blood pressure, temperature, pulse rate and blood oxygenation. Accordingly, the VSM preferably includes at least a microprocessor, a memory, and input and output ports or channels for sending and receiving data to the various sensors as well as to other devices, including data storage devices at locations remote from the VSM. The VSM memory, in addition to being capable of storing data generated by the processor or received via the input port(s), is used to store instructions including commands and processes followed by the processor. Specifically, the VSM preferably includes software and/or firmware, stored in the VSM memory and executed by the VSM microprocessor, that controls functions of the VSM as well as helps to regulate interactions of the VSM with the various sensors attached to the VSM and other external devices. The VSM memory is preferably digital memory capable of storing digitized data. The VSM memory is also preferably at least partially comprised of non-volatile digital memory.

The input and output ports, or communications port(s), of the VSM can preferably send and receive data to and from the VSM by either wired or wireless transmission or a combination of the two and can handle and produce either digital or analog data. Examples of different types of communications ports used in the VSM of the present invention include, but are not limited to, serial ports (e.g., various types registered jack ports such as RJ11 or RJ45 format using RS232, IEEE 802.3, or other similar communication standards), universal serial bus (USB) ports, and radio frequency (RF) network interface controllers with their associated antennas (hereinafter, wireless ports), in addition to the various types of input ports used in connecting the above-noted sensors to the VSM. Where appropriate, the communications ports of the VSM are preferably capable of interacting with and transmitting data between a number of different other devices connected through direct hard-wired connections or any type of network, including, for example, local area networks (LAN), personal area networks (PAN) and the Internet. If wireless transmission of data is implemented through a wireless port, it is preferable that the VSM include hardware that allows it to communicate wirelessly using any desired or appropriate protocol. Examples of protocols that could be used by the VSM to communicate wirelessly through a communication port include, but are not limited to, the Wireless Medical Telemetry Bands, in the 608-614 MHz, 1395-1400 MHz, or 1427-1432 MHz ranges, as well as ZigBee®, Bluetooth®, or IEEE 802.11 communication protocols.

In certain embodiments of the present invention the VSM preferably has more than one input and/or output port(s). In embodiments of the present invention in which the VSM uses multiple communications ports, it is not required that all ports be of the same type. For example, in certain preferred embodiments, the VSM may have multiples of each of USB ports, Ethernet ports, serial ports, and wireless ports, or such other ports as may be desirable for communication of analog or digital data. Multiple communications ports allow the VSM to both send and receive information more effectively and efficiently as well as to easily communicate with numerous different devices. By way of example, one can envision an instance in which the VSM is simultaneously receiving data from physiological sensors connected to the VSM, processing this data, then communicating this data to an external storage location using radio frequency communication.

In embodiments of the present invention in which the VSM is used to measure blood pressure, the VSM preferably includes a pump capable of using atmospheric air to pressurize a sphygmomanometer cuff to pressures sufficient for accurate measurement of human systolic and diastolic brachial artery blood pressures. Blood pressure measurement is preferably performed using pressure sensors pneumatically connected with the sphygmomanometer cuff and accompanying algorithms executed by the VSM processor that can determine a subject's blood pressure without the need of a stethoscope and without requiring significant clinician involvement.

In embodiments of the present invention in which the VSM is capable of measuring pulse rate or blood oxygenation, these measurements are preferably accomplished using a transmission-based infrared oximeter sensor connected to the processing system of the VSM. However, in other preferred embodiments of the present invention, measurement of blood oxygenation and pulse rate can be accomplished using a reflectance-based infrared oximeter sensor used on the forehead or other appropriate location. It will further be noted that in still other embodiments of the present invention, measurement of pulse rate need not be accomplished using an oximeter sensor, but can instead be accomplished using the above-mentioned sphygmomanometer cuff and associated pressure sensors.

In embodiments of the present invention in which the VSM is capable of measuring temperature, temperature measurement is preferably accomplished using a thermistor-based temperature probe that is capable of measuring a subject's temperature using either axillary or oral placement of the temperature probe. In still other preferred embodiments temperature can be measured from a subject using temporal artery or tympanic membrane temperature probes connected to the processing system of the VSM.

Certain embodiments of the VSM can include a display screen for displaying data to the user of the VSM. Data that can be displayed on the screen of the VSM includes the measurements obtained using any of the above-noted physiological sensors or information from other diagnostic devices such as devices for recording electrocardiogram signals from a subject or devices such as spirometers used to measure a subject's pulmonary or respiratory function. Because the VSM can connect to other devices over the types of networks mentioned above, data displayed on the screen of the VSM can also include data pertaining to a subject's health, such as data obtained from the subject's medical records, including data relating to medical problems previously experienced by the subject.

The display screen of the VSM can be either liquid crystal display (LCD) or light emitting diode (LED) based, or a combination of the two. Thus, in various embodiments, the display screen of the VSM can be a passively lit monochrome LCD display, a backlit color LCD display (including the use of LEDs for backlighting), or an LED-only display, including the use of organic LEDs. In addition, the display screen of the VSM can also be a touch-sensitive display screen. A touch-sensitive display screen allows the user to manipulate data that is displayed on the screen and can also allow the user to add additional data to a subject's medical record, or add additional details to the physiological measurements collected from the subject using the VSM. A touch-sensitive display screen also allows the user to easily adjust the system settings of the VSM (e.g. units in which measurements are displayed). If a touch-sensitive screen is implemented, it can be either a capacitance-based touch-sensitive screen or a resistance-based touch-sensitive screen. In still other embodiments, the VSM may receive user input such as that described above via a keyboard, mouse, or other independent input device attached to the VSM. In this case, a display screen would be required on the VSM, however, this display screen would not need to be touch-sensitive since data entry and manipulation of data, or changing the type of data displayed, could be accomplished using the independent input means just noted.

In embodiments of the present invention in which the VSM does not include a display screen, the VSM can preferably connect to a personal computer through one of the communication ports listed above. In this embodiment the personal computer preferably includes appropriate software to allow it to effectively communicate with and transfer data between the VSM. Also in this embodiment, the display of the personal computer can be used to display data collected by the VSM, and the keyboard, mouse, or other input means attached to the personal computer can be used to manipulate this data, add additional data to a subject's medical record, add additional details to the physiological measurements collected from the subject using the VSM, or change the VSM settings. In addition to the physiological sensors noted above, the VSM can further preferably accept input from other outside devices. By way of specific example, it is preferable that the VSM be capable of communicating with the exam table of the present invention. More specifically, it is preferable that the VSM be capable of receiving subject weight measurements generated by the exam table and subsequently displaying the weight measurement on the display screen (whether built-in display or the display of a personal computer to which the VSM is connected) of the VSM. Such a feature is advantageous because it eliminates the need for a separate display for displaying weight in the exam room, and, more importantly, allows for automatic recording of a subject's weight without needing to manually enter this data. Further, in instances in which the VSM is also connected to the electronic medical record system of an organization, the VSM can allow the subject's weight to be automatically recorded in the subject's electronic medical record. Other independent devices that can be attached or connected to the VSM include devices for sensing and measuring cardiac function, such as an ECG device, as well as devices for measuring respiratory or pulmonary function, such as a spirometer. If such devices are connected to the VSM, the VSM can preferably display data produced by such devices and also store this data, or, where desired, transfer this data for recording in the electronic medical record system of the organization in which the VSM is used.

In addition to the VSM being able to accept input from various sensors and devices, it is also preferable that the VSM be able to output data to other devices in order to allow the VSM to act as a control point within an examination room or clinical space. By way of specific example, the VSM of the present invention is preferably able to output data and commands to the exam table of the present invention in such a way as to control the position of the exam table. More specifically, it is preferable that the VSM be able to control the movement and positioning of exam tables of the present invention that are adjustable using power-driven adjustment. By controlling the movement and positioning of the exam table it is meant that a user can position the exam table by inputting the desired table movement or position into the VSM. Accordingly, in embodiments of the present invention in which the VSM is capable of controlling exam table position, it is preferable that a user can control the position of the exam table by inputting a desired position via a touch-sensitive screen integrated with the VSM. While use of a touch-screen integrated with the VSM is the most preferable approach, other preferred embodiments can allow a user to adjust table position using an independent input device (e.g. keyboard, mouse, or personal computer) connected to the VSM. Using the VSM to control position of the exam table is advantageous because it can lead to increased efficiency in care delivery in the clinical setting by allowing a clinician to accomplish multiple tasks from a single position, or single touch point, within the examination room or clinical space. Use of the VSM to control table position is further advantageous because the VSM can include pre-programmed table positions that allow one to efficiently collect physiological data from a subject. For example, the VSM can include a preset table position to be used in obtaining a blood pressure measurement from a subject. Thus, use of this preset position would automatically position the subject with the correct back incline, foot position, arm position, etc. needed to accurately and efficiently obtain a blood pressure measurement from a subject using the VSM. As a specific example, the VSM could be preprogrammed to position the exam table so that the subject is positioned in accordance with the American Heart Association guidelines for in-clinic blood pressure measurement, which would include ensuring the subject is in a position in which the subject's back is supported, legs uncrossed and upper arm supported at approximately heart level. As an additional example, the VSM could include a preprogrammed position for performing ECG measurement on a subject, which would include automatic movement of the exam table to a supine position. Other preset positions could include low, semi-, standard, and high Fowler's positions as well as sitting and Trendelenburg positions. Furthermore, in still other embodiments, the VSM could be programmed with a set of user-specified preprogrammed positions that could be varied based upon the specific needs of the individual user.

It will be noted that connection of the VSM to other devices as well as to the physiologic sensors described above, can be done using either hard-wired or wireless connections of the types previously described herein.

In addition to the above-noted features, the VSM preferably also includes a power source for powering the processing system of the VSM as well as providing power, where needed, to the sensors and/or other devices used in combination with the VSM. The power source can include line voltage (e.g. 120V, 60 Hz A/C; 220V, 50 Hz A/C) filtered through appropriate regulators, or can include a rechargeable battery that is charged by the use of appropriate regulators connected to line voltage. If a rechargeable battery is used, it is preferably a nickel-cadmium, nickel-metal hydride, lithium-ion, or lithium-ion polymer battery.

Additionally, as briefly mentioned above, in certain preferred embodiments of the present invention the VSM includes hardware and software that allow the VSM to connect to and interact with the electronic medical record (EMR) system of the facility in which the VSM is located. In this way, the VSM can both retrieve existing data from, and send newly recorded data to, the EMR system of the facility. By providing the ability to electronically record and transfer physiological measurement data, the VSM can eliminate the time-consuming manual entry of such data into an EMR system.

The above description of the preferred embodiments has been largely focused on description of the individual elements of the invention. However, figures are useful in gaining a greater understanding of the way in which the various elements of the present invention interact and interrelate to produce many of the methods and techniques encompassed within the present invention. To this end, a number of illustrative figures are discussed in greater detail below.

Turning now to a description of FIG. 1, there is shown a perspective view of one embodiment of the exam table 10 of the present invention. The exam table shown in FIG. 1 is adjustable in both height of the sitting area 14 and angle of the back support 12. The sitting area 14 and back support 12 of the exam table are illustrated in FIG. 1 as being upholstered. Addition of upholstery to the exam table provides increased comfort for patients as well as aesthetic benefits to the clinical space in which the exam table is placed. The exam table illustrated in FIG. 1 further includes extendable tool trays 16 for use during examinations or in-office procedures. Also shown is a drawer 18 for supply storage in addition to a button 20 that can be depressed to activate operation of a heated seating area and/or heated drawer area. A heated drawer area is advantageous in that it can warm treatment and examination supplies to a comfortable temperature in order to lessen patient discomfort when the supplies are used in the treatment or examination process. The exam table 10 further includes a table base 22, which provides stability to the exam table and a point of contact between the exam table and the surface on which the exam table is placed. A telescopic exam table shell cover 28 is also connected to the exam table base 22. The telescopic cover 28 serves to cover the hardware that is used to adjust the exam table height and angle of the exam table back support 12, and thus prevent patients or users from inadvertently damaging or interfering with the table hardware and adjustment mechanisms. Adjustment of the exam table 10, illustrated in FIG. 1 can be accomplished using handheld control 60, and/or foot control 24. Both handheld control 60 and foot control 24 are illustrated as wireless, meaning they are able to connect to and control movement of the exam table 10 without the need of wires. However, it will be understood that in other embodiments of the present invention, handheld control 60 and foot control 24 can be connected to exam table 10 with the use of appropriate wires. Foot control 24 is used to control movement and adjustment of the exam table 10 by accepting input via the user input buttons 23 located on the foot control. Thus, if a user desires to adjust or move the exam table using the foot control, the user simply uses his or her foot to depress the input button 23 that is assigned to the desired movement. The handheld control 60 operates in a similar manner, accepting input from a user's fingers. The handheld control is described in greater detail in the description of FIG. 6 below.

Figure 2:
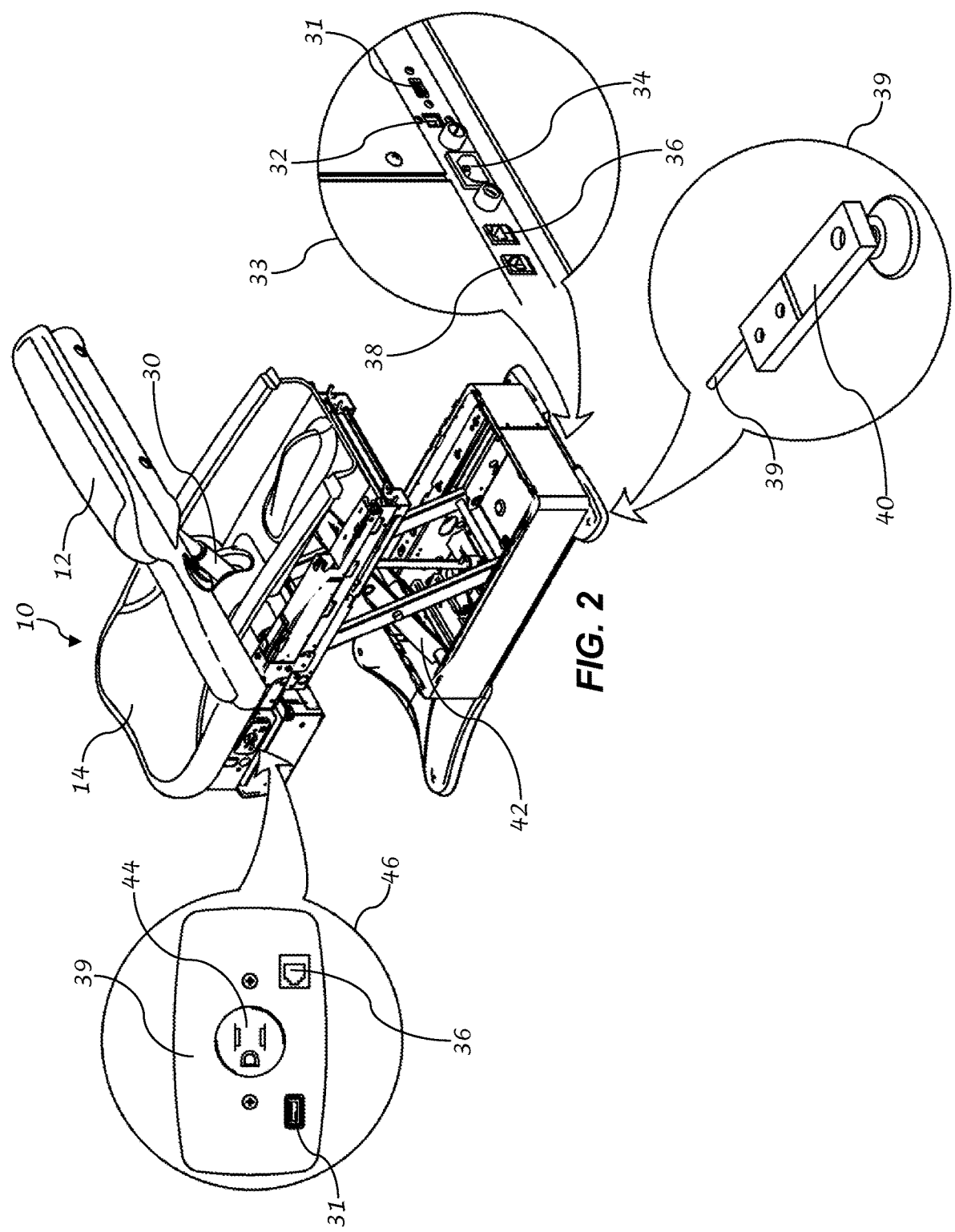
FIG. 2 Perspective drawing of one embodiment of the exam table of the present invention showing various features of the exam table in greater detail.

In FIG. 2 is shown a rear perspective view of the embodiment of the exam table 10 illustrated in FIG. 1. In FIG. 2, the telescopic cover 28 of the exam table hardware is partially removed, allowing one to see the scissors mechanism 42 that is used to adjust height of exam table 10. In actual use, there is preferably an actuator connected to the scissors mechanism and that is used to extend and retract the scissors mechanism as the table height is respectively increased and decreased. The back support actuator 30 is also illustrated in FIG. 2. As back support actuator 30 is extended the back support 12 is forced into a more upright position. When back support actuator 30 is retracted, back support 12 is lowered into a more supine position. FIG. 2 also provides a magnified view of several features of the exam table 10. In magnified view 33, there is shown a number of communications ports and a power port, located at the lower rear portion of the exam table. Specifically, the lower rear portion of the exam table includes a Type A USB port 31, a Type B USB port 32, and two registered jack ports 36, 38. The lower rear portion of the exam table further includes a line voltage port 34 for connecting line voltage to the exam table. Registered jack ports 36, 38 and USB ports 31, 32 can be utilized for a number of purposes that involve the transfer of data to or from the exam table 10. By way of example, the Type A or Type B USB ports 31, 32 can be used for connecting a personal computer to the exam table, while the registered jack ports 36, 38 can be used for connecting items to the table such as a VSM (described in greater detail below) or a wired handheld or foot control. In still other situations, and by way of further example, the Type A USB port 31 could be used to connect a diagnostic device such as a spirometer to the table.

In magnified view 39 of FIG. 2, there is shown an example of a load sensor 40 used in combination with exam table 10 to obtain a subject's weight when the subject is seated on the table. The load sensor 40 is illustrated as being positioned in a corner of the exam table. Thus, in the embodiment of the exam table illustrated in FIG. 2 it is preferable that four such load sensors be positioned in the exam table with one load sensor located at or near each corner of the exam table. Load sensor 40 further includes load sensor connecting wire 39 used to connect the load sensor to the processing system of the exam table.

In magnified view 46 of FIG. 2, there is shown an example of a connection panel 39 in which power and communications ports are grouped together in a single small panel near the front of the exam table to provide convenient access to these ports. In the embodiment of the connection panel 39 shown in magnified view 46, the panel includes a Type A USB port 31, a registered jack port 36, and a standard line voltage power connection 44. Preferably Type A USB port 31 is also powered and can, if needed, provide low voltage direct current power to device attached thereto. Line voltage power connection 44 can be utilized to power a number of devices that may be used in conjunction with exam table 10, including examination lights, surgical tools, and personal computers, among others. As before, the Type A USB port 31 and registered jack port 36 can be utilized for a number of purposes that involve the transfer of data to or from the exam table 10, including, for example, connecting a personal computer, diagnostic device, VSM, or handheld or foot control to the exam table.

Figure 3:
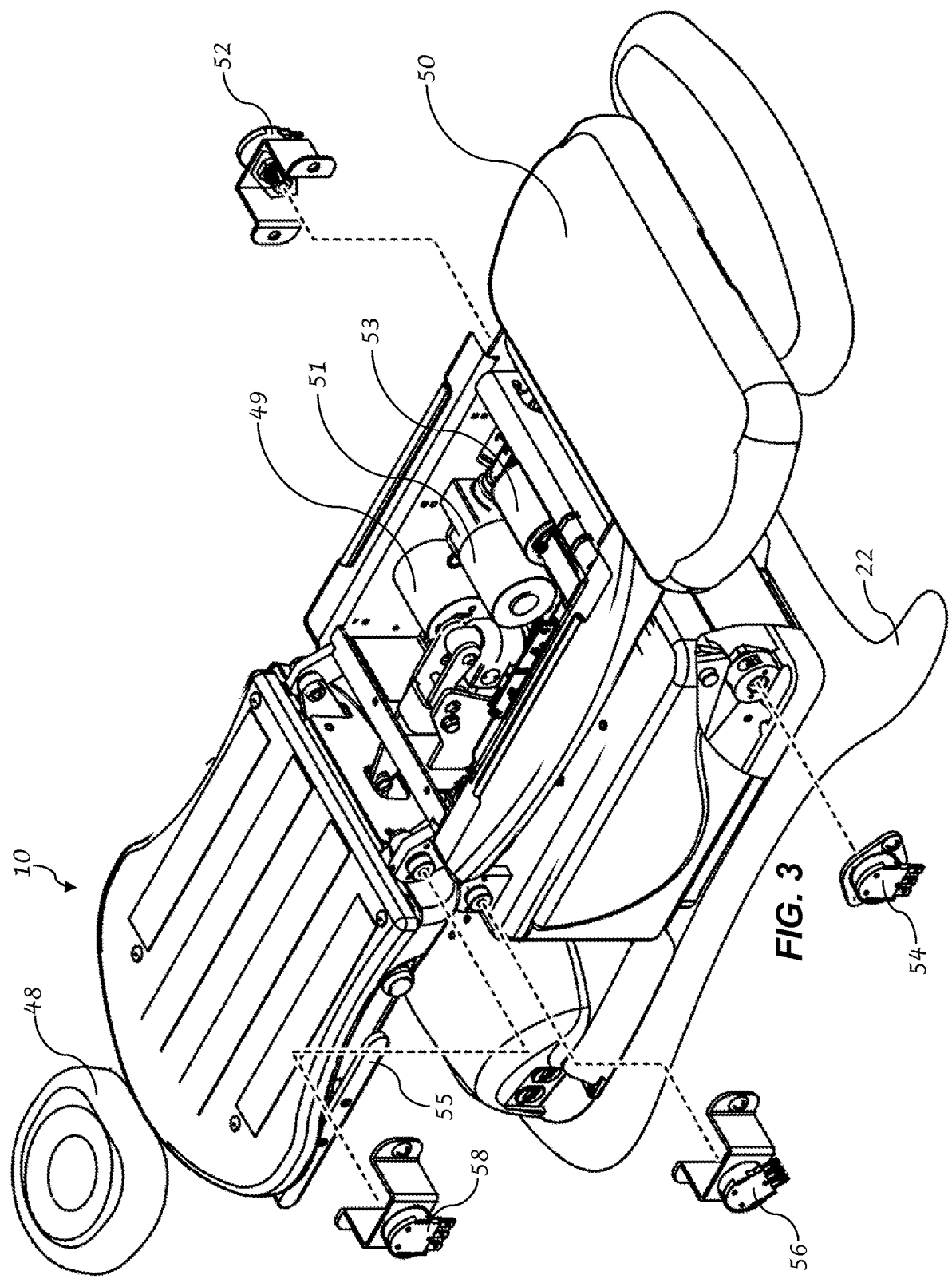
FIG. 3 Perspective drawing of one embodiment of the exam table of the present invention illustrating, among other features, the location of limit switches and actuators used in controlling position of the exam table.

Turning now to a description of FIG. 3, there is shown another embodiment of the exam table 10 of the present invention. In contrast to the embodiment of the exam table shown in FIG. 1 and FIG. 2, the embodiment shown in FIG. 3 includes an adjustable patient head support 48 and an adjustable patient foot support 50. The presence of an adjustable head support 48 and adjustable foot support 50 can increase the overall functionality of the exam table and increase the utility of the exam table for use in simple outpatient surgical procedures or examination procedures that require a higher degree of versatility in patient positioning. The exam table 10 illustrated in FIG. 3 further includes siderail 55 which can serve as a mounting or support point for table accessories such as armboards for positioning a patient's arm while the patient is seated on the exam table, surgical instruments, lighting, or other accessories used in procedures or examinations. Also illustrated in FIG. 3 are limit switches 52, 54, 56, 58, which serve to stop movement of the exam table 10 beyond certain points determined by the limit switch settings. Specifically, limit switch 52 limits movement of the adjustable foot support 50, limit switch 54 serves to limit adjustment of table height, limit switch 56 limits the elevation angle (or degree of incline) of the sitting area of the exam table, and limit switch 58 limits degree of incline of the back support area of the exam table. FIG. 3 further illustrates the location of several linear actuators 49, 51, 53 that are used in controlling adjustment of the exam table. In particular, linear actuator 49 controls the elevation angle of the sitting area of the exam table, linear actuator 51 controls adjustment of the foot support 50, and linear actuator 53 controls the degree of incline of the back support area. The head support 48 of the embodiment of the exam table illustrated in FIG. 3 is manually adjustable.

Figure 4:
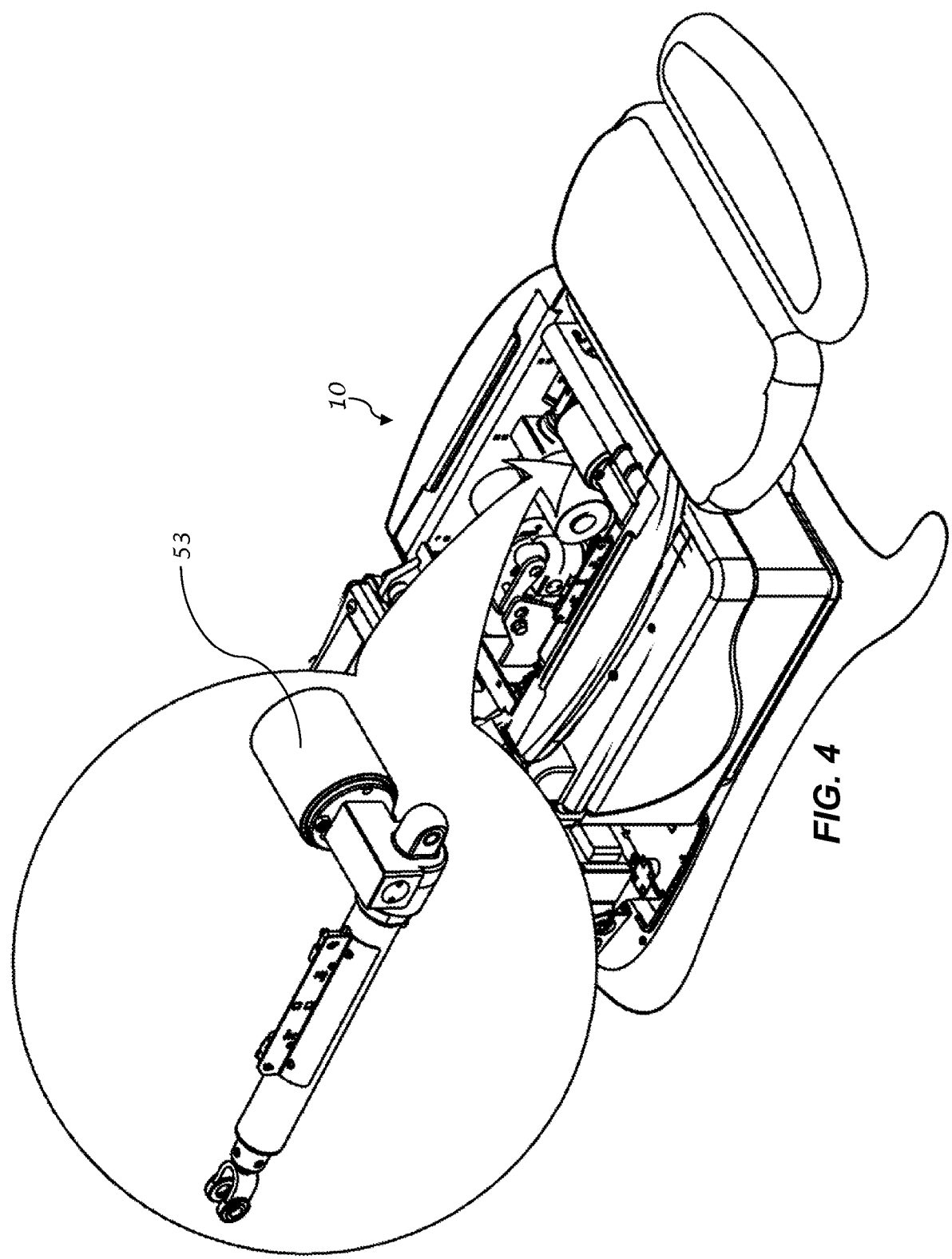
FIG. 4 Perspective drawing of one embodiment of the exam table of the present invention providing a detailed view of one of the table actuators.

In FIG. 4 a magnified view of the back support linear actuator 53 used in adjusting the degree of incline of the back support area of the exam table illustrated in FIG. 3 is shown. This magnified view illustrates how the linear actuator is oriented within the table housing and provides a clear illustration of the overall form of the linear actuator.

Figure 5:
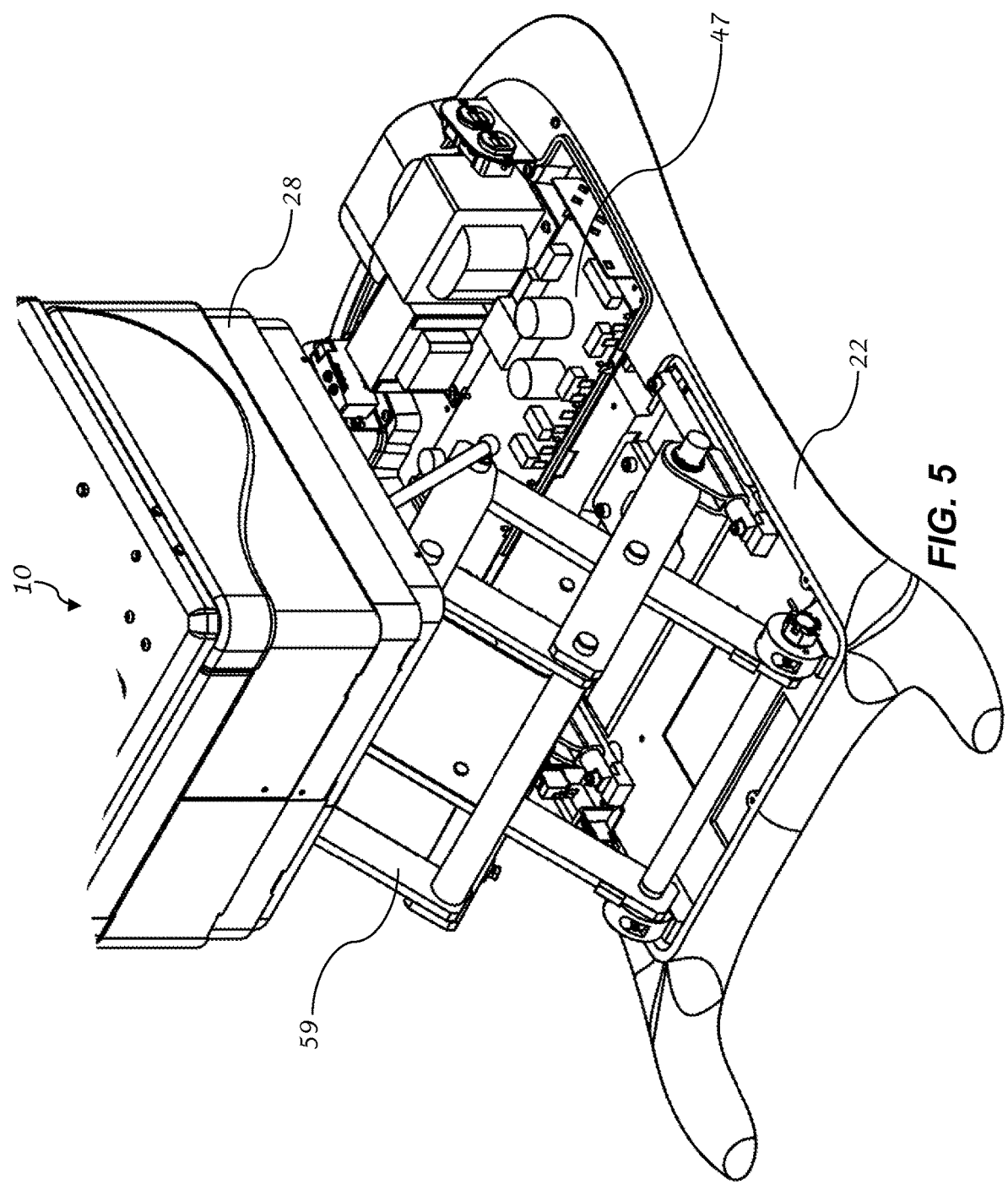
FIG. 5 Perspective drawing of a portion of one embodiment of the exam table of the present invention illustrating structural and other features of the exam table.

Turning now to a description of FIG. 5, there is shown close-up view of the scissors mechanism 59 and other hardware included in the embodiment of the exam table 10 illustrated in FIG. 3. The scissors mechanism is preferably connected to a linear actuator (not shown), which, when extended causes an increase in exam table height and when retracted leads to a decrease in exam table height. Also shown in FIG. 5 is a printed circuit board 47 attached to the base 22 of the exam table. While specific features of the printed circuit board 47 are not discussed in reference to FIG. 5, it will be understood that the printed circuit board 47 generally serves as the processing system of the exam table and thus includes at least a processor, digital memory, and input and/or output port(s).

Figure 6:
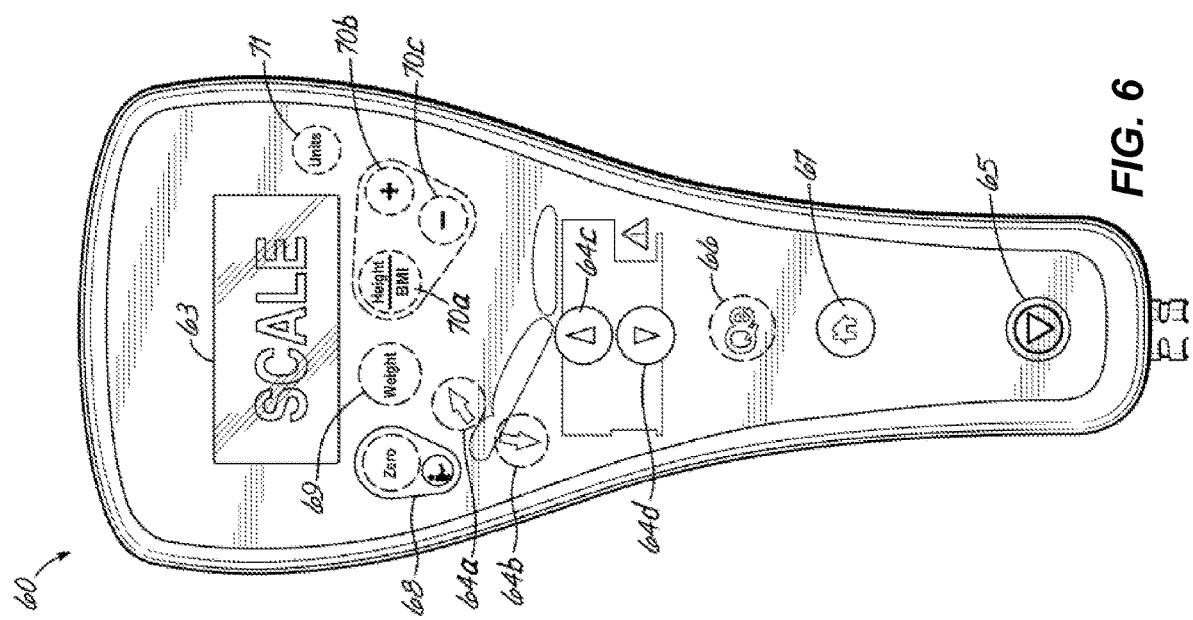
FIG. 6 A detailed view of a handheld control used in certain embodiments of the present invention to position the exam table.

FIG. 6 shows a detailed view of one embodiment of a handheld control 60 used in the present invention to control table position. The handheld control includes controls for the scale function of the exam table as well as controls for positioning/adjusting the exam table. Specifically, the handheld control includes a number of buttons that can be depressed by a user in order to cause the exam table to perform certain functions. The handheld control also includes a weight display screen 63 for displaying the weight of a subject seated on the table as measured using the load sensors of the exam table. The weight display screen 63 can be either a color or monochrome liquid crystal display. If a color liquid crystal display is used, it is preferably backlit using light emitting diodes.

Among the features provided by handheld control 60 are adjustment of degree of incline of the back support of the exam table 64a, 64b and adjustment of the height of the sitting area of the exam table 64c, 64d. The handheld control can also include preset positions such as a "home" position button 67, which, when selected causes the exam table to return to an upright seated position used for convenient ingress and egress to and from the exam table. Optional preset exam table positions can also include a "Quick Exam" button 66 that can be preset by a user to a position frequently used in administering examinations. The use of such preset table positions can greatly increase efficiency within a clinical space since automatic adjustment of the exam table frees the clinician to perform other tasks during the time that would otherwise be spent adjusting the exam table. Also illustrated as a feature of handheld control 60 is a stop button 65, which can be selected to stop movement of the exam table at any time. For example if one of the above-mentioned preset positions is initially selected and the user then changes his or her mind about use of the preset position, the user can simply select the stop button 65 to stop the automatic positioning of the table and return full control of table position to the user.

Handheld control 60 can also include features for controlling and managing the scale function of the exam table. For example, a taring, or "zero" button 68, can be selected in order to tare the scale function of the table, while the weight button 69 can be selected to initiate acquisition of the weight of a subject seated on the exam table. Units in which weight is displayed on the weight display screen 63 can be selected using the units button 71. For example, selection of the units button 71 can cause the units in which weight is displayed to toggle between pounds and kilograms, or other desired units. Still more sophisticated functions can be provided by the handheld control 60 such as the calculation of a subject's body mass index. For example if a user knows a subject's height, the user can select the "Height/BMI" button 70a and then use "+" and "−" buttons 70b, 70c to input a subject's height in either inches or centimeters. A processor included in the handheld control, or the processing system of the exam table can then use the weight measured by the load sensors of the exam table along with the entered height in order to reach a calculation of a subject's body mass index and display that value on the weight display screen 63 of the handheld control 60.

Figure 7:
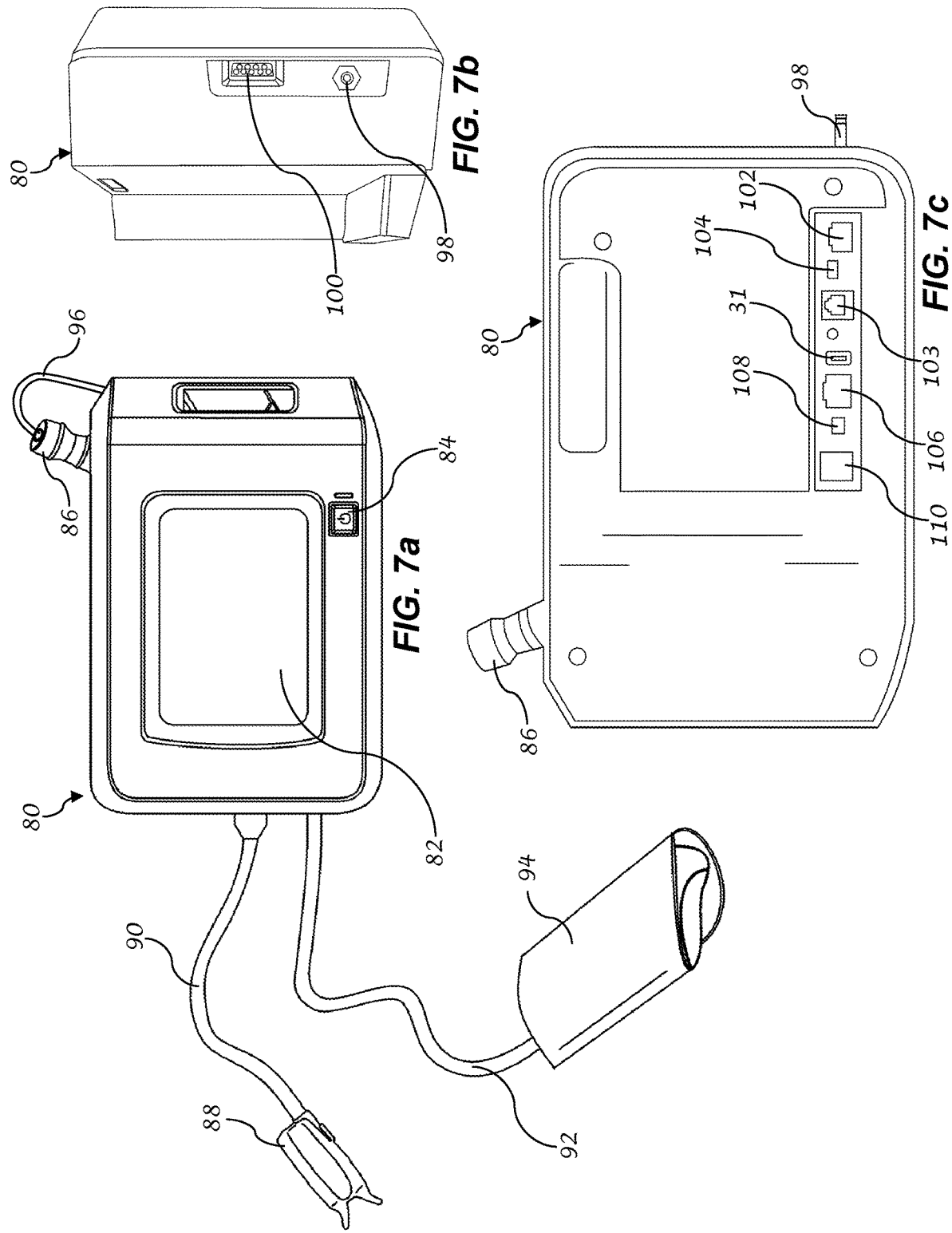
FIG. 7a-c Various views of one embodiment of the vital signs monitor of the present invention, illustrating certain features thereof.

Turning now to a description of FIG. 7a-c, there are shown multiple views of one embodiment of the VSM 80 of the present invention. In FIG. 7a there is shown a front view of the VSM. The embodiment of the VSM shown preferably includes the ability to obtain blood pressure measurements. Accordingly, the VSM includes a sphygmomanometer cuff 94 that is attached to the VSM via a hose 92 through which air is passed from the VSM 80 to the sphygmomanometer cuff 94 in order to pressurize the cuff. The VSM is also preferably capable of measuring blood oxygenation and pulse rate using a transmission-based fingertip pulse oximetry sensor 88, connected to the VSM via pulse oximetry cable 90. Still further, the VSM depicted in FIG. 7a-c is preferably capable of measuring a subject's temperature using temperature probe 86. Temperature probe 86 can be any type of probe including those capable of measuring temperature using the temporal artery or tympanic membrane, in addition to more traditional temperature probes used in oral or axillary temperature measurement. The VSM further includes a display screen 82 for displaying information to the user, including the results of physiological measurements obtained using the above-mentioned sensors. The display screen 82 in the embodiment shown in FIG. 7a is further preferably a touch-sensitive color LCD or LED display. FIG. 7a further illustrates power switch 84 that can be selected by a user to activate or deactivate the VSM.

FIG. 7b shows a side view of the VSM 80, and illustrates the location of the pulse oximetry sensor port 100, and the pneumatic port 98 for connection of the sphygmomanometer cuff 94.

FIG. 7c shows a back view of the VSM 80, illustrating a number of communications ports and connections that can be utilized by the VSM. Specifically, the embodiment of the VSM illustrated in FIG. 7c includes a first registered jack port 102, a mini USB port 104, a second registered jack port 103, a Type A USB port 31, a third registered jack port 106, a power input port for providing an outside source of power to the VSM, and a temperature probe port 110 for connection of the temperature probe 86 to the VSM. By way of example, but not limitation, the above-noted ports could be configured as follows: first registered jack port 102 could be used to connect the VSM to an external printer for printing paper copies of data stored on or obtained using the VSM; second registered jack port 103 could be used to connect the VSM to the exam table of the present invention in order to receive and display weight measurements produced by the exam table and in order to allow a user to control exam table position via the VSM; mini USB port 104 could be used to connect the VSM to a personal computer; Type A USB port 31 could be used to connect a device for measuring a subject's ECG signals to the VSM; and third registered jack port 106 could be used to connect the VSM to a computer network using, for example, an RJ45 connector attached to a length of Category 5 cable. While numerous other configurations are possible, the example provided should be sufficient to illustrate the capabilities and features of the VSM of the present invention to those of ordinary skill in the art.

Figure 8:
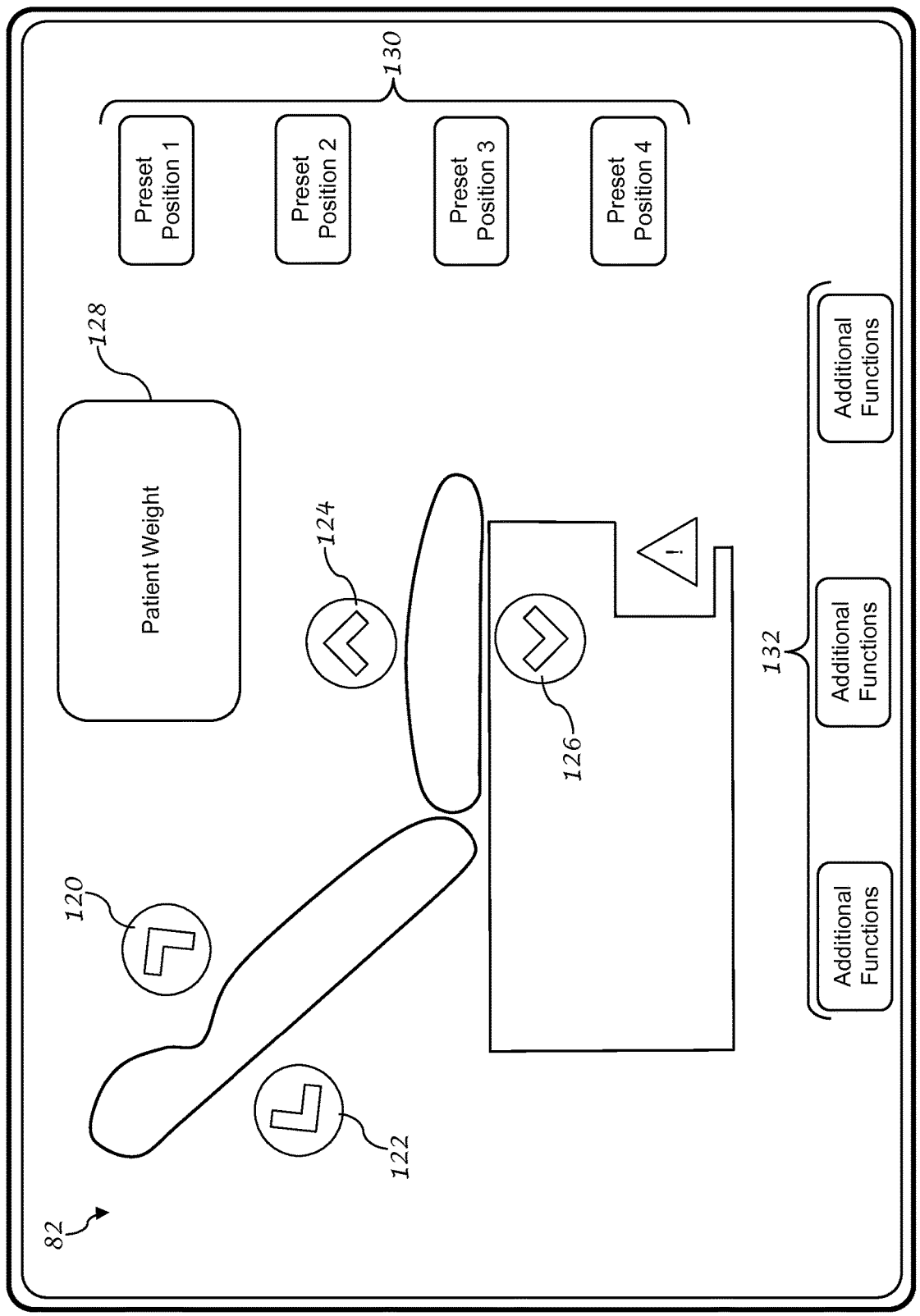
FIG. 8 A exemplary representation of a vital signs monitor user interface screen for controlling the position of the exam table of the present invention.

Turning now to FIG. 8 there is shown one example of how a touch-sensitive VSM display screen of the present invention may appear to a user who is using the VSM to control function and position of the exam table of the present invention. In this example, the display screen includes an area for displaying a patient's weight 128, as well touch points for controlling the degree of incline of the exam table back support 120, 122 and the height of the exam table sitting area 124, 126. For example, if a user were to touch to the display screen at touch point 126, the exam table would receive a command via the VSM causing it to decrease in height. In this example the VSM display screen also includes a number of preprogrammed or user-programmable preset positions 130. Such preset positions could include, for example, positions for used measuring ECG from a subject, having a subject perform a spirometry test, or acquiring a subject's blood pressure. Thus, by touching the VSM display screen at one of the preset position touch points, the user can cause the exam table to automatically move to a desired preset position, such a supine position used for measuring electrocardiogram signals from a subject. Finally, this example includes a number of touch points on the display screen that allow the user to access additional functions 132 or move to different menus of the VSM. Examples of additional functions include VSM settings, display of physiological data recorded by the VSM sensors, historical views of data obtained using the VSM, and the like. It will be understood that FIG. 8 is exemplary only and that other structures and layouts are possible using the VSM display screen. For example, a patient's weight need not necessarily be displayed on the table adjustment interface screen but could instead be displayed on a separate interface screen showing other information such as data collected using the physiological sensors of the VSM.

Figure 9:
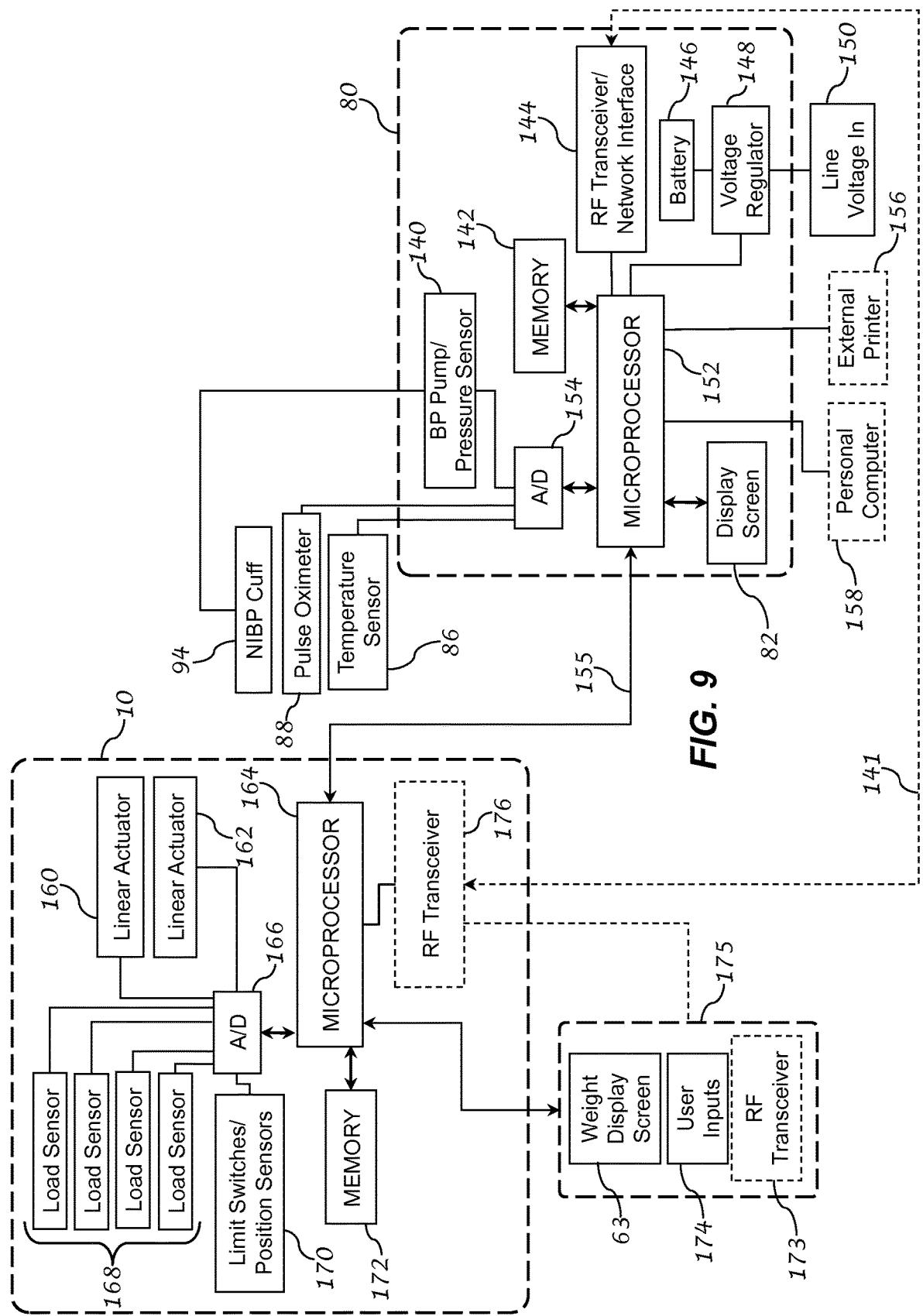
FIG. 9 A schematic block diagram illustrating a number of components of the exam table and vital signs monitor of the present invention.

Turning now to a description of FIG. 9, there is shown a schematic block diagram illustrating various components of the VSM and exam table that are included in certain preferred embodiments of the present invention. The components included within the exam table are located within box 10. Likewise the components included within the VSM of the present invention are located within box 80.

The exam table 10 includes a number of load sensors 168, which are connected to the table converter 166, which, in turn, is capable of converting analog data to digital data, and vice versa. Linear actuators 160, 162, used to adjust the position of the exam table, are also connected to the table converter 166. Table converter 166, is further illustrated as accepting input from limit switches and other position sensors 170. It will be understood by those of ordinary skill in the art that the use of digital sensors negates the need for conversion of analog signals to digital format. Thus, those of ordinary skill in the art will understand that in other embodiments of the exam table of the present invention one could use, for example, digital limit switches and eliminate the need for analog to digital conversion of the limit switch signal. In similar fashion, individual components (e.g. individual load sensors or linear actuators) can be individually equipped with analog to digital/digital to analog converters and thus eliminate the need for the shared table converter 166 shown in FIG. 9.

Once digitized, the signals from the various sensors and actuators of the exam table of the present invention are collected by the exam table processor 164, and processed/ handled in accordance with processing instructions stored in the exam table memory 172. Exam table memory 172 can also be used to store data collected from table sensors for later use or analysis. The exam table microprocessor 164 can further accept input and provide output to an external control device 175. For example, the exam table microprocessor can accept data from the load sensors 168, process this data to obtain a subject's weight, then pass the subject's weight to the external control device 175 for display on a weight display screen 63. In turn, the external control device 175 can accept various user inputs 174 and communicate these inputs to the exam table microprocessor 164, which can then issue commands, for example, to the linear actuators 160, 162 and initiate movement of the exam table. The exam table 10 and external control device 175 can each optionally include an RF transceiver 176, 173, which, as illustrated, can be used to allow wireless data transfer between the exam table 10 and the external control device 175, and thus wireless control of the exam table.

Similar to exam table 10, VSM 80 includes a VSM memory 142, which stores instructions to be followed by VSM microprocessor 152 and can also store data collected from the various physiological sensors used with the VSM, or data received from exam table 10. In FIG. 9, temperature sensor 86 and pulse oximeter sensor 88 are connected to VSM microprocessor 152 via VSM converter 154. VSM converter 154 is preferably capable of converting analog data to digital data, and vice versa. The non-invasive blood pressure cuff (or sphygmomanometer cuff) 94 is pneumatically connected to a blood pressure pump 140 used to pressurize the blood pressure cuff 94. Blood pressure pump 140 further preferably includes, or is connected to, pressure sensors and other sensors used to obtain a blood pressure measurement. Like the pulse oximeter sensor 88 and temperature sensor 86, blood pressure sensor 140 is connected to VSM converter 154. As with exam table 10, those of ordinary skill in the art will understand that use of fully digital sensors can eliminate the need for analog to digital conversion of sensor signals and thus eliminate the need for VSM converter 154. VSM microprocessor 152 is further preferably connected to the VSM display screen 82. If VSM display screen 82 is a touch sensitive screen, microprocessor can preferably not only send data to the VSM screen 82 but also receive input from the VSM display screen 82. The VSM microprocessor can further optionally communicate with an external personal computer 158 and/or an external printer 156.

The VSM preferably receives power by a line voltage connection 150 that is regulated by at least one voltage regulator 148. However, the VSM can also rely on a battery 146 as a power source. Reliance on battery power is advantageous because it allows the VSM to be highly portable. While the voltage regulator 148 is shown in FIG. 9 as being connected only to VSM microprocessor 152, it will be understood by those of ordinary skill in the art that voltage regulator 140 can be configured to produce a number of different power outputs connected to a number of different components. By way of example, the power requirements of blood pressure pump 140 are likely to be very different than the power requirements of the VSM microprocessor 152. Accordingly, though not illustrated in FIG. 9, separate power connections from the blood pressure pump 140 and the microprocessor 152 to the voltage regulator 148 would likely be necessary.

The VSM 80 further preferably includes an RF transceiver/network interface 144 that allows the VSM to both receive data wirelessly as well as be connected to networks of other computing devices. As illustrated by dashed line 141, in embodiments of the present invention in which the exam table 10 includes an RF transceiver 176 the VSM RF transceiver 144 can be used to wirelessly communicate with the exam table 10, and thus wirelessly control the position of exam table 10. In embodiments in which exam table 10 does not include an RF transceiver 176, communication between the VSM and RF transceiver can be accomplished via a hard wired connection, illustrated by solid line 155.

Figure 10:
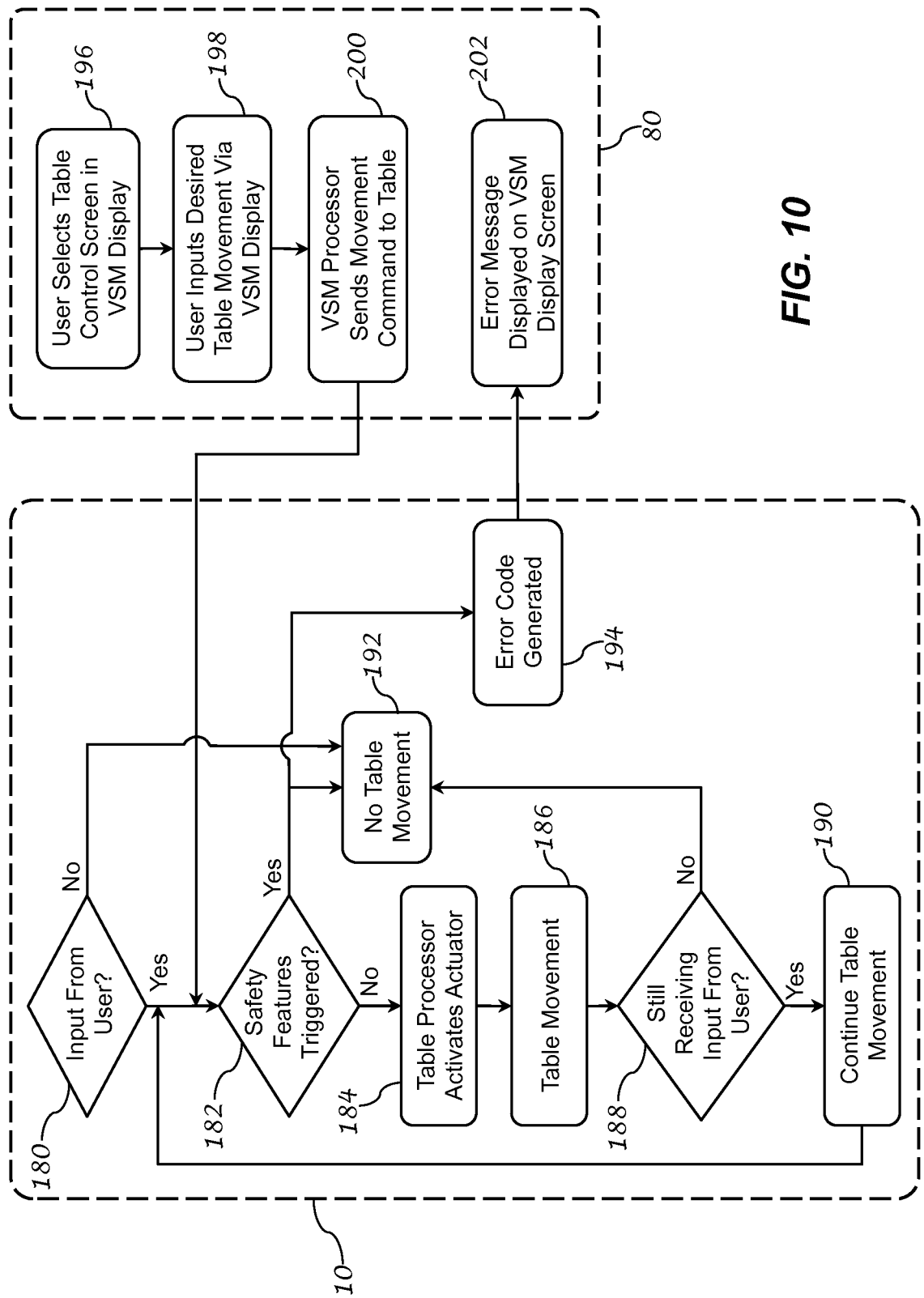
FIG. 10 A flow diagram illustrating an exemplary exam table control process that can be implemented as part of the present invention.

In FIG. 10 is shown a flow diagram illustrating one exemplary control process that can be used in the present invention. Specifically, FIG. 10 illustrates control of the exam table 10 of the present invention with the VSM 80. As with FIG. 9, the processes conducted within the exam table are located within box 10 of FIG. 10. Likewise steps or processes included within the VSM of the present invention are located within box 80 of FIG. 10.

In the control process shown in FIG. 10, the exam table 10 receives input from a user 180. In this instance input from the user is generated via a touch-sensitive screen included in the VSM 80. Specifically, one uses the touch-sensitive screen of the VSM to first navigate to the table control screen in the VSM display 196. From there the user inputs desired table movement via the touch-sensitive screen of the VSM 198, after which the VSM processor sends the desired movement command 200 to the processing system of the exam table 10 Once input from a user is received, the processing system of the exam table checks whether any of the safety features of the exam table have been triggered 182. Safety features include, among other items, table position sensors, limit switches or sensors for measuring resistance to movement experienced by one of the table actuators. If the exam table processing system determines that safety features have been triggered no table movement occurs 192 and an error code is generated 194 and subsequently sent to the VSM 80 and displayed on the VSM screen 202. If the exam table processing system finds that no safety features have been triggered, the processing system sends the appropriate signal to the appropriate table actuator 184 and the exam table begins to move 186. If the exam table continues to receive an input signal from the user 188 the table movement continues 190. Once the table movement signal from the user ceases 188, the processing system of the exam table generates appropriate commands to stop table movement 192.

In FIG. 11-16 there are shown several flow diagrams illustrating data movement between various parts of the present invention. In each of FIG. 11-16 a sensor suite 210 comprising a noninvasive blood pressure sensor 94, a pulse oximeter sensor 88, and a temperature sensor 86, sends data to the vital signs monitor 80 of the present invention. Likewise, in each of FIG. 11-16 a power-adjustable exam table 10 with an integrated scale exchanges data with other components or elements of the present invention. EMR system 214 as depicted in FIG. 11-16 includes the electronic medical record system of the facility in which the exam table 10 and vital signs monitor 80 are located or the electronic medical record system managed by the clinician providing care to a patient using the exam table 10 and vital signs monitor 80 of the present invention. The cloud figure shown in FIG. 11-16 is intended to represent the Internet or other communication system 212 by which digital data can be moved to a location or locations remote from the site of patient care or treatment.

In FIG. 11 is shown an embodiment of the present invention in which the VSM 80 includes software and appropriate hardware that allow the VSM to communicate directly with the EMR system 214. Such an arrangement is desirable in certain instances because it allows physiological measurements obtained using sensor suite 210 to be directly transferred to a patient's electronic medical record using only the VSM. Likewise, the VSM 80 can capture the weight obtained from the load sensors of the exam table 10 and directly transfer this to a patient's electronic medical record.

In the embodiment illustrated in FIG. 11, the VSM can also be used to control exam table position. Use of the VSM in this manner is advantageous because it can increase efficiency for the clinician since it allows the clinician to easily record and input patient data into the EMR system and also control the examination table from a single point in the examination or treatment room. FIG. 11 further illustrates one approach by which the Internet or other communication system 212 can be structured and used to efficiently move data from the VSM 80 to the EMR system 214. Specifically, in FIG. 11, the VSM interfaces with a thin client terminal 211. In turn, the thin client terminal, receives information and transmits information to the PC/server 213, which processes information received from the VSM 80 via the thin client terminal 211 and sends this information back to the VSM 80 via the thin client terminal 211 or else sends the processed information on to the EMR system 214 via a network to which both the PC/Server 213 and the EMR system 214 are connected. The PC/Server 213 can also receive and/or retrieve data from the EMR system and subsequently send this data to the VSM via the thin client terminal 211. It will be noted, however, that use of a thin client terminal 211 is not required in all embodiments of the present invention and further that Internet or other communication system 212 as illustrated in FIG. 11 is not required to include the use of PC/Server 213. Rather, this is only one exemplary method of accomplishing communication between the VSM 80 or personal computer 158 and the EMR system 214.

FIG. 12 is largely identical to FIG. 11, however, in FIG. 12 a personal computer 158 serves as a connection point between VSM 80 and the EMR system 214. Thus, in the embodiment of the present invention illustrated in FIG. 12, the VSM does not need to include the software and hardware necessary to communicate with the EMR system 214. Rather, this software and appropriate hardware is located on the personal computer 158. While data obtained using the sensor suite 210 and data received from the exam table 10 are initially handled by the VSM 80, the ultimate communication of this data to the EMR system 14 is handled by the personal computer 158.

FIG. 13 includes the addition of the hand or foot control 60, 24, discussed in detail above, to control exam table position. Thus, FIG. 13 illustrates the fact that in certain embodiments of the present invention the exam table 10 can accept input from, and output data to, more than one control device. For example, in the embodiment illustrated in FIG. 13, a clinician may view a subject's weight measurement produced by the exam table on the weight display screen 63 of the handheld control 60, while at the same time the VSM 80 can capture this weight and transmit the weight to the EMR system for recording in the subject's electronic medical record.

FIG. 14 illustrates an embodiment of the present invention in which the VSM acts only as a data processor and transmits this data to a personal computer 158. Specifically, in the embodiment of the present invention shown in FIG. 14, the personal computer 158 includes software and hardware that allow it to connect to and control the exam table 10 as well as to interface and exchange data with the EMR system 214. Accordingly, the VSM 80 of FIG. 14 preferably does not include a display screen since VSM data can simply be displayed on the display of the personal computer 158.

Figure 15:
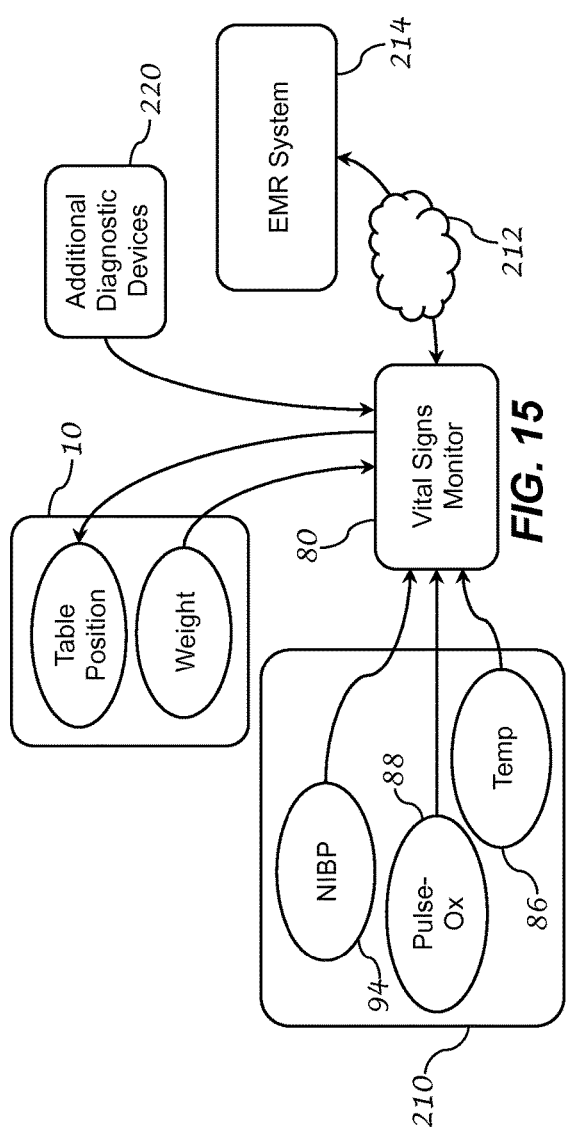
FIG. 15 A flow diagram illustrating one method of data movement between various elements of the present invention.

FIG. 15 illustrates an embodiment of the present invention in which the VSM 80 is capable of directly accepting input from additional diagnostic devices 220. Such additional diagnostic devices can include, for example, devices for measuring a subject's ECG signals or devices such as a spirometer for measuring a subject's respiratory function. Accordingly, in the embodiment of the present invention illustrated in FIG. 15, the VSM is preferably capable of displaying data collected using the additional diagnostic devices 220 as well as optionally processing this data and/or sending the data to the EMR system 214 for recording. Further, in the embodiment of the present invention illustrated in FIG. 15, the VSM preferably includes preset table positions for automatically placing a subject seated on the exam table in a position ideally suited for using an additional diagnostic device to collect data from the subject. In this way, use of additional diagnostic devices with the exam table of the present invention can be accomplished easily and efficiently.

Figure 16:
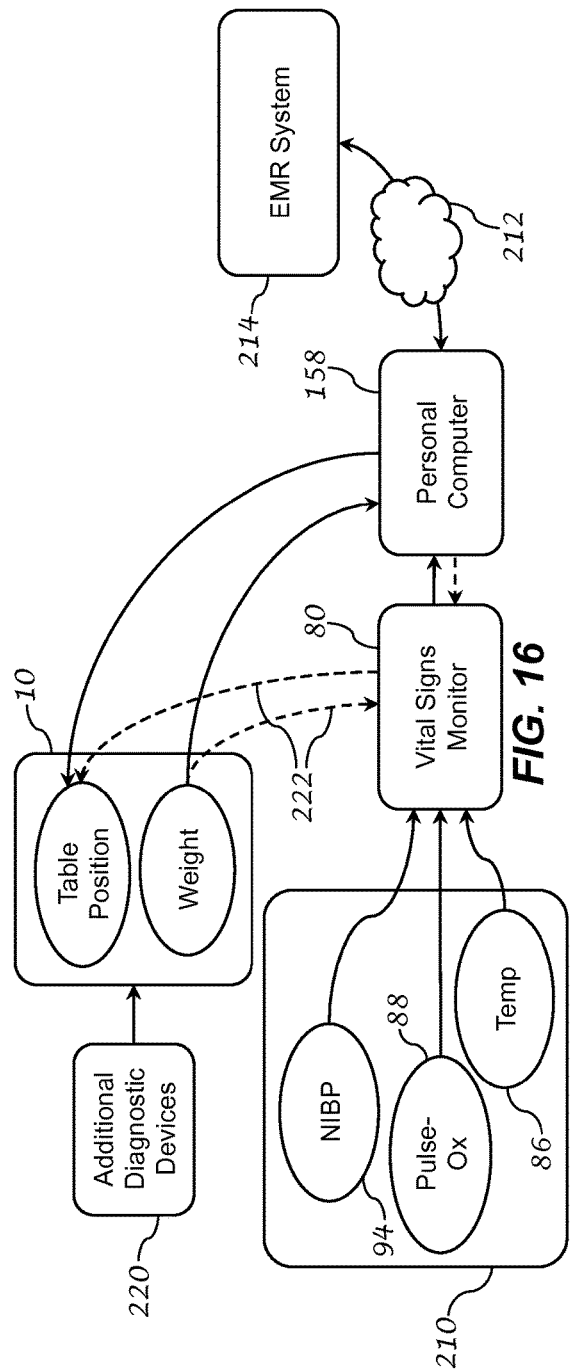
FIG. 16 A flow diagram illustrating one method of data movement between various elements of the present invention.

Turning now to FIG. 16 there is shown an additional embodiment of the present invention in which the exam table 10 is capable of accepting input from and connecting to additional diagnostic devices 220. In this embodiment, the exam table 10 is connected to a personal computer 158. The personal computer 158 in this embodiment preferably includes software and hardware sufficient to allow the personal computer to not only control position of and accept weight measurements from the exam table, but also to accept and process data from the additional diagnostic devices and subsequently communicate this data to the EMR system 214. Alternatively, as illustrated by dashed lines 222, control of the exam table, input of weight measurements obtained from the exam table, and handling of data acquired using the additional diagnostic devices 222, can be performed by the VSM 80, with this data ultimately being communicated to the EMR system using personal computer 158.

It will be apparent to those skilled in the art that various modifications and variations can be made to the present invention without departing from the spirit and scope of the invention as set forth in the above description. Thus, it is intended that the present invention cover the modifications and variations of this invention provided they come within the scope of the invention and its equivalents.

What we claim is:

1. A system for improving an efficiency of data collection in a clinical space, the system comprising:
   (a) a stationary exam table resting on a surface, the exam table comprising:
      (i) a base, wherein the base is configured to rest on the surface,
      (ii) a telescopic exam table shell cover connected to the base,
      (iii) a back support, wherein the back support is adjustable at an angle relative to the surface,
      (iv) a sitting area adjustable at a height relative to the surface, wherein the angle of the back support and the height of the sitting area are independently adjustable,
      (v) a handheld control device, wherein the handheld control device is configured to selectively adjust the angle of the back support, wherein the handheld control device is configured to selectively adjust the height of the sitting area, (vi) an input channel, wherein the input channel k configured to receive a movement command from a secondary control device and actuate the exam table to adjust one or both of the angle of the back support and the height of the sitting area in accordance with the movement command, (vii) a drawer having a heated drawer area, (viii) a button, wherein the button is configured to be depressed to activate heating of the heated drawer area, (ix) at least one load sensor for sensing a weight measurement of a subject seated on the exam table, wherein the at least one load sensor is disposed in the base, wherein the at least one load sensor comprises a series of resistors arranged in a Wheatstone bridge configuration, (x) at least one output channel for outputting the weight measurement; and (b) a vital signs monitor electronically connected to the exam table as the secondary control device, the vital signs monitor comprising:

(i) at least one input channel for accepting signals from at least one physiological sensor, (ii) at least one output channel for sending the signals to the exam table, and (iii) a touch-sensitive display screen for receiving the movement command from a user and for displaying information obtained from the at least one physiological sensor, (iv) a microprocessor, (v) a digital memory for storing instructions to be executed by the microprocessor, and (vi) an additional input channel for accepting the weight measurement;

wherein:

(1) the vital signs monitor is configured to transmit the movement command via the output channel to the input channel of the exam table to adjust one or both of the angle of the hack support and the height of the sitting area;

(2) the microprocessor and the memory of the vital signs monitor are configured to:

A. automatically store the weight measurement in an electronic medical record associated with the subject in an electronic medical records system; and B. automatically store in the electronic medical record associated with the subject at least one preset position to which the exam table can be automatically moved in response to a user input on the touch-sensitive display screen, wherein the preset position includes a first angle for the angle of the back support and a first height for the height of the sitting area.

2. The system of claim 1 wherein the exam table and the vital signs monitor each further comprise a radio frequency transceiver and wherein an electronic connection between the power-adjustable exam table and the vital signs monitor is a wireless connection.

3. The system of claim 1 wherein the exam table comprises a first actuator configured to adjust the angle of the back support and a second actuator configured to adjust the height of the sitting area.

4. The system of claim 1 wherein the at least one physiological sensor is a blood pressure sensor.

5. The system of claim 4 wherein the vital signs monitor further comprises two additional input channels for accepting signals from a pulse oximeter sensor and a temperature sensor, wherein the vital signs monitor is configured to display a set of oxygen data from the pulse oximeter sensor and a set of temperature data from the temperature sensor via the touch-sensitive display screen.

6. The system of claim 1 wherein the at least one preset position is a position optimal for non-invasively measuring a subject's blood pressure.

\* \* \* \* \*